(12) United States Patent
Pekari et al.

(10) Patent No.: US 7,517,986 B2
(45) Date of Patent: Apr. 14, 2009

(54) TETRAHYDROPYRIDOTHIOPHENES FOR USE IN THE TREATMENT OF CANCER

(75) Inventors: Klaus Pekari, Radolfzell (DE); Thomas Baer, Reichenau (DE); Mathias Schmidt, Constance (DE); Thomas Beckers, Constance (DE)

(73) Assignee: 4SC AG, Planegg Martinsrid (DE)

( * ) Notice: Subject to any disclaimer, the term of this patent is extended or adjusted under 35 U.S.C. 154(b) by 38 days.

(21) Appl. No.: 11/597,556

(22) PCT Filed: Jun. 3, 2005

(86) PCT No.: PCT/EP2005/052570

§ 371 (c)(1),
(2), (4) Date: Nov. 27, 2006

(87) PCT Pub. No.: WO2005/118592

PCT Pub. Date: Dec. 15, 2005

(65) Prior Publication Data

US 2007/0213360 A1    Sep. 13, 2007

(30) Foreign Application Priority Data

Jun. 4, 2004   (EP) .................. 04102531

(51) Int. Cl.
C07D 471/02 (2006.01)
(52) U.S. Cl. .................................. 546/114
(58) Field of Classification Search .............. 546/114
See application file for complete search history.

(56) References Cited

U.S. PATENT DOCUMENTS

| | | | |
|---|---|---|---|
| 4,963,559 A | 10/1990 | Suzuki | |
| 5,422,335 A | 6/1995 | Hagen et al. | |
| 2003/0232994 A1 | 12/2003 | Lu et al. | |

FOREIGN PATENT DOCUMENTS

| | | | |
|---|---|---|---|
| DE | 272 078 A1 | 9/1989 | |
| DE | 40 39 734 A1 | 6/1992 | |
| WO | 98/02440 A1 | 1/1998 | |
| WO | 99/46267 A1 | 9/1999 | |
| WO | 02/092076 A1 | 11/2002 | |
| WO | 2004/024065 A2 | 3/2004 | |
| WO | 2004/024066 A2 | 3/2004 | |
| WO | 2004/069149 A2 | 8/2004 | |
| WO | 2004/092156 A1 | 10/2004 | |
| WO | 2005/033102 A2 | 4/2005 | |
| WO | 2005/044008 A2 | 5/2005 | |
| WO | 2005/060711 A2 | 7/2005 | |
| WO | 2005/118071 A2 | 12/2005 | |
| WO | 2005/120642 A2 | 12/2005 | |

OTHER PUBLICATIONS

Fujita et al. (Bioorganic &Medicinal Chemistry Letters (2002), 12, 1897-1900.*
Database Chemcats, Chemical Abstracts Service, Columbus, Ohio, US; XP002303659; abstract & "Ambinter Screening Library", Jan. 1, 2004.
Database Chemcats, Chemical Abstracts Service, Columbus, Ohio, US; XP002369767; abstract & "Interchim Intermediates", Jan. 18, 2005.
Database Chemcats, Chemical Abstracts Service, Columbus, Ohio, US; XP002369768; abstract & "Ambinter Stock Screening Collection", Jul. 3, 2005.
Database Chemcats, Chemical Abstracts Service, Columbus, Ohio, US; XP002361378; abstract & "Interchim Intermediates", Jan. 18, 2005.
Database Chemcats, Chemical Abstracts Service, Columbus, Ohio, US; XP002303660; abstract & "TimTec Overseas Stock", Jun. 1, 2004.
Database Chemcats, Chemical Abstracts Service, Columbus, Ohio, US; XP002361377; abstract & "Ambinter Screening Library", Jan. 1, 2004.

* cited by examiner

*Primary Examiner*—D. Margaret Seaman
*Assistant Examiner*—Nizal S Chandrakumar
(74) *Attorney, Agent, or Firm*—Millen, White, Zelano & Branigan, P.C.

(57) ABSTRACT

Compounds of the formula (I)

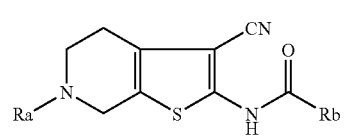

in which Ra and Rb have the meanings indicated in the description, are novel effective compounds with anti-proliferative and/or apoptosis inducing activity.

18 Claims, No Drawings

TETRAHYDROPYRIDOTHIOPHENES FOR USE IN THE TREATMENT OF CANCER

This application was filed under 35 U.S.C. 371 as a national stage of PCT/EP2005/052570, filed Jun. 3, 2005.

FIELD OF APPLICATION OF THE INVENTION

The invention relates to heteroarylamido-substituted tetrahydropyridothiophene derivatives, which can be used in the pharmaceutical industry for the production of pharmaceutical compositions. The invention further relates to the contribution made to the art by the finding, that said tetrahydropyridothiophene derivatives display cell-cycle dependent, antiproliferative and apoptosis inducing activity.

The invention also relates to the use of these compounds for the therapy of hyperproliferative diseases, in particular human cancer.

KNOWN TECHNICAL BACKGROUND

Cancer chemotherapy was established with the alkylating agent Cyclophosphamide (Endoxan® oxazaphosphorin prodrug activated preferentially in the tumor. The target of alkylating agents like Cyclophosphamide is DNA and the concept, that cancer cells with uncontrolled proliferation and a high mitotic index are killed preferentially, proved to be very successful. Standard cancer chemotherapeutic drugs finally kill cancer cells upon induction of programmed cell death ("apoptosis") by targeting basic cellular processes and molecules. These basic cellular processes and molecules include RNA/DNA (alkylating and carbamylating agents, platin analogs and topoisomerase inhibitors), metabolism (drugs of this class are named anti-metabolites and examples are folic acid, purin and pyrimidine antagonist) as well as the mitotic spindle apparatus with αβ-tubulin heterodimers as the essential component (drugs are categorized into stabilizing and destabilizing tubulin inhibitors; examples are Taxol/Paclitaxel®, Docetaxel/Taxotere® and vinca alkaloids).

A subgroup of proapoptotic anticancer agents target cells preferentially in mitosis. In general these agents do not induce apoptosis in non-dividing cells, arrested in the G0, G1 or G2 phase of the cell division cycle. In contrast, dividing cells going through mitosis (M-phase of the cell division cycle), are killed efficiently by induction of apoptosis by this subgroup agents. Therefore, this subgroup or class of anti-cancer agents is described as cell-cycle specific or cell-cycle dependent. Tubulin inhibitors, with Taxol (Paclitaxel®) as a prominent example, belong to this class of cell-cycle specific, apoptosis inducing anti-cancer agents.

PRIOR ART

The international application WO2004/024065 mentions, inter alia, arylamido-substituted tetrahydropyridothiophene derivatives as glucagon antagonists for the treatment of diabetes. The international application WO20041024066 mentions, inter alia, arylamido-substituted tetrahydrobenzothiophene derivatives as glucagon antagonists for the treatment of diabetes.

The german document DE4039734 describes, inter alia, N-alkylated tetrahydropyridothiophene derivatives as components of herbicidal agents.

The german document DD272078 describes, inter alia, N-alkylated tetrahydropyridothiophene derivatives with antianaphylactic und antihistaminergic properties.

The international application WO02/092076 is directed to substituted coumarins and quinolines as caspase activators.

The U.S. patent US4963559 relates to 5-(2-chlorobenzyl)-4,5,6,7-tetrahydro-thieno[3,2-c]pyridine as an agent for treating cancer and preventing cancer metastasis.

DESCRIPTION OF THE INVENTION

It has now been found that the heteroarylamido-substituted tetrahydropyridothiophene derivatives, which are described in greater details below, differ from prior art compounds by creative structural alterations and have surprising and particularly advantageous properties.

In more detail, it has been unexpectedly and unanticipatedly found that the tetrahydropyridothiophene derivatives, which are described in greater details below, are potent and highly efficadious cell-cycle specific inducers of apoptosis in cancer cells. Therefore, yet unanticipatedly, these tetrahydropyridothiophene derivatives are useful for treating (hyper) proliferative diseases and/or disorders responsive to the induction of apoptosis, in particular cancer. By having a cell-cycle specific mode of action, these tetrahydropyridothiophene derivates should have a higher therapeutic index compared to standard chemotherapeutic drugs targeting basic cellular processes like DNA replication or interfering with basic cellular molecules like DNA Thus, for example, the compounds according to this invention are expected to be useful in targeted cancer therapy.

The invention thus relates in a first aspect (aspect 1) to compounds of formula I

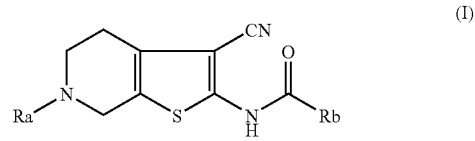

wherein
Ra is —C(O)R1, —C(O)OR2, —C(O)SR2, —C(O)N(R3)R4, —S(O)₂R1, or —S(O)₂N(R3)R4; and either
Rb is optionally substituted by Rca and/or Rcb, and is Har, or
Rb is Cyc, or
Rb is chromenyl;

in which
R1, R2 and R3 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R5;
each R4 is independently selected from the group consisting of: hydrogen, 1-7C-alkyl, or 3-7C-cycloalkyl, wherein each of said 1-7C-alkyl and 3-7C-cycloalkyl can be unsubstituted or optionally substituted by at least one substituent independently selected from R5;
R5, Rca and Rcb may be the same or different and are independently selected from the group consisting of: 1-7C-alkyl, 3-7C-cycloalkyl, Ar, Har, Het, halogen, trifluoromethyl, nitro, cyano, guanidino, amidino, —C(O)R6, —C(O)OR7, —C(O)N(R8)R9, —S(O)₂R6, —S(O)₂N(R8)R9, —N(R10)C(O)R6, —N(R10)C(O)OR7, —N(R10)C(O)N(R8)R9, —N(R10)S(O)₂R6, —N(R10)S(O)₂N(R8)R9, —OC(O)R6, —OC(O)N(R8)R9, —OR7, —N(R8)R(9), or —SR7, wherein each of said 1-7C-alkyl, 3-7C-cycloalkyl, Ar, Har and Het can be unsubstituted or optionally substituted by at least one substituent independently selected from R11;

R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or optionally substituted by at least one substituent independently selected from R12;

each R9 is independently selected from the group consisting of: hydrogen, 1-7C-alkyl, or 3-7C-cycloalkyl, wherein each of said 1-7C-alkyl and 3-7C-cycloalkyl can be unsubstituted or optionally substituted by at least one substituent independently selected from R12;

each R10 is independently selected from the group consisting of: hydrogen, 1-7C-alkyl, or 3-7C-cycloalkyl;

R11 is selected from the group consisting of: R5 as defined above;

each R12 is independently selected from the group consisting of: R5 as defined above;

each Ar is independently selected from phenyl and naphthyl;

each Har is independently any fully aromatic or partially aromatic mono- or fused bicyclic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzo group, any 3-7C-cycloalkane group as defined herein, any additional heteroaryl ring A as defined herein afore, or any heterocyclic ring B as defined herein below, whereby said Har ring or ring system is attached to the parent molecular group via a substitutable ring carbon or ring nitrogen atom;

each Het is independently any fully saturated or partially unsaturated mono- or fused bicyclic ring or ring system made up of a first constituent being a 3- or 7-membered monocyclic fully saturated or partially unsaturated, non-aromatic heterocyclic ring B, which heterocyclic ring B comprises one to three heteroatoms independently selected from nitrogen, oxygen and sulfur, and which heterocyclic ring B is optionally substituted by one or two oxo groups, and, optionally, fused to said first constituent, a second constituent being a benzo group, any 3-7C-cycloalkane group as defined herein, or any additional heterocyclic ring B as defined herein afore, whereby said Het ring or ring system is attached to the parent molecular group via a substitutable ring carbon or ring nitrogen atom;

Cyc is a group of formula W

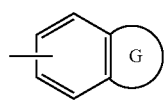

in which

G is optionally substituted by Rda and/or Rdb on a ring carbon atom, and is a 5- or 6-membered saturated heterocyclic ring comprising one or two heteroatoms independently selected from the group consisting of —N(Rdc)—, oxygen and sulfur, in which Rda is 1-4C-alkyl, or halogen, Rdb is 1-4C-alkyl, or halogen, each Rdc is independently selected from the group consisting of: hydrogen, 1-4C-alkyl, and 1-4C-alkylcarbonyl, whereby said Cyc ring system is attached to the parent molecular group via a substitutable benzoring carbon atom;

and the salts, solvates or the solvates of the salts thereof.

As used herein, "alkyl" refers to both branched and straight chain saturated aliphatic hydrocarbon groups having the specified numbers of carbon atoms, such as for example: 1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

1-7C-Alkyl is a straight-chain or branched alkyl radical having 1 to 7 carbon atoms. Examples are the heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals. An embodiment of 1-7C-alkyl, 1-6C-alkyl or 1-5C-alkyl refers to 1-4C-alkyl, such as e.g. methyl, ethyl, propyl or butyl.

One notable embodiment of herein-mentioned "alkyl" having the specified numbers of carbon atoms refers to the straight-chain radicals thereof.

3-7C-Cycloalkyl stands for cyclopropyl, cyclobutyl, cyclopentyl, cyclohexyl and cycloheptyl, of which cyclopropyl and cyclopentyl are to be emphasized.

3-7C-Cycloalkane stands for cyclopropane, cyclobutane, cyclopentane, cyclohexane and cycloheptane, of which cyclohexane and cyclopentane are to be emphasized.

3-7C-Cycloalkyl-1-4C-alkyl stands for one of the abovementioned 1-4C-alkyl radicals, which is substituted by one of the abovementioned 3-7C-cycloalkyl radicals. Examples which may be mentioned are the 3-7C-cycloalkylmethyl radicals (such as e.g. cyclopropylmethyl or cyclohexylmethyl) and the cyclohexylethyl radical.

Halogen within the meaning of the present invention is iodine, or, particularly, bromine, chlorine or fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radicals.

2-4C-Alkoxy represents radicals which, in addition to the oxygen atom, contain a straight-chain or branched alkyl radical having 2 to 4 carbon atoms. Examples which may be mentioned are the butoxy, isobutoxy, sec-butoxy, tert-butoxy, propoxy, isopropoxy and preferably the ethoxy radical.

1-4C-Alkoxy-2-4C-alkoxy stands for one of the abovementioned 2-4C-alkoxy radicals which is substituted by one of the abovementioned 1-4C-alkoxy radicals. Examples which may be mentioned are the 2-(methoxy)ethoxy (—O—CH$_2$—CH$_2$—O—CH$_3$) and the 2-(ethoxy)ethoxy radical (—O—CH$_2$—CH$_2$—O—CH$_2$—CH$_3$).

Phenyl-1-4C-alkoxy represents one of the abovementioned 1-4C-alkoxy radicals, which is substituted by a phenyl radical. Examples which may be mentioned are the phenethoxy and the benzyloxy radicals.

1-4C-Alkylcarbonyl represents a radical which, in addition to the carbonyl group, contains one of the abovementioned 1-4C-alkyl radicals. An example which may be mentioned is the acetyl radical.

1-4C-Alkoxycarbonyl represents a radical which, in addition to the carbonyl group, contains one of the abovementioned 1-4C-alkoxy radicals. Examples which may be mentioned are the methoxycarbonyl, the ethoxycarbonyl and the tertbutoxycarbonyl radicals.

1-4C-Alkylcarbonyloxy radicals contain, in addition to the oxygen atom, one of the abovementioned 1-4C-alkylcarbonyl radicals. An example is the acetoxy radical ($CH_3C(O)$—O—).

In addition to the nitrogen atom, mono- or di-1-4C-alkylamino radicals contain one or two of the abovementioned 1-4C-alkyl radicals. Di-1-4C-alkylamino is preferred and here, in particular, dimethyl-, diethyl- or diisopropylamino.

Mono- or Di-1-4C-alkylaminocarbonyl radicals contain in addition to the carbonyl group one of the abovementioned mono- or di-1-4C-alkylamino radicals. Examples which may be mentioned are the N-methyl- the N,N-dimethyl-, the N-ethyl-, the N-propyl-, the N,N-diethyl- and the N-isopropylaminocarbonyl radical.

An 1-4C-Alkylcarbonylamino radical is, for example, the propionylamino ($C_3H_7C(O)NH$—) and the acetylamino radical ($CH_3C(O)NH$—).

(1-4C-Alkoxy-2-4C-alkoxy)-2-4C-alkoxy represents 2-4C-alkoxy radicals, which are substituted by one of the abovementioned 1-4-alkoxy-2-4C-alkoxy radicals. Examples which may be mentioned are the 2-(2-methoxyethoxy)-ethoxy and the 2-(2-ethoxyethoxy)-ethoxy radicals.

As it is known for the skilled person, the terms imidazolo, pyrazolo, piperidino or morpholino stands for imidazol-1-yl, pyrazol-1-yl, piperidin-1-yl or morpholin-4-yl, respectively. Similar terms used herein are to be understood similarly, mutatis mutandis, as defined for these terms.

The term (R5)-methyl stand for methyl which is substituted by R5. The term 2-(R5)-ethyl stands for ethyl which is substituted in 2-position by R5. The term 3-(R5)-propyl stands for propyl which is substituted in 3-position by R5.

Ar stands for naphthyl or, particularly, phenyl.

Har stands for a fully aromatic or partially aromatic mono- or fused bicyclic ring or ring system made up of a first constituent being a 5- or 6-membered monocyclic unsaturated, aromatic heteroaryl ring A, which heteroaryl ring A comprises one to four heteroatoms independently selected from nitrogen, oxygen and sulfur, and, optionally, fused to said first constituent, a second constituent being a benzo group, a 3-7C-cycloalkane group as defined herein, an additional heteroaryl ring A as defined herein afore, or a heterocyclic ring B as defined herein below in the context of the definition of Het, whereby said Har ring or ring system is attached to the parent molecular group via a substitutable ring carbon or ring nitrogen atom of any of said constituents.

Examples for Har may include, but are not limited to, 5-membered heteroaryl radicals, such as e.g. furanyl, thiophenyl, pyrrolyl, oxazolyl, isoxazolyl, thiazolyl, isothiazolyl, imidazolyl, pyrazolyl, triazolyl, thiadiazolyl, oxadiazolyl, and 6-membered heteroaryl radicals, such as e.g. pyridinyl, pyrimidinyl, pyrazinyl or pyridazinyl, and the benzo-fused derivatives thereof such as e.g. quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl, benzimidazolyl, benzotriazolyl, benzoxadiazolyl or benzothiadiazolyl, as well as naphthyridinyl, indolizinyl or purinyl.

Het stands for a fully saturated or partially unsaturated mono- or fused bicyclic ring or ring system made up of a first constituent being a 3- or 7-membered monocyclic fully saturated or partially unsaturated, non-aromatic heterocyclic ring B, which heterocyclic ring B comprises one to three heteroatoms independently selected from nitrogen, oxygen and sulfur, and which heterocyclic ring B is optionally substituted by one or two oxo groups, and, optionally, fused to said first constituent, a second constituent being a benzo group, a 3-7C-cycloalkane group as defined herein, or an additional heterocyclic ring B as defined herein afore, whereby said Het ring or ring system is attached to the parent molecular group via a substitutable ring carbon or ring nitrogen atom of any of said constituents.

Examples for Het may include, but are not limited to, aziridinyl, azetidinyl, pyrrolidinyl, piperidinyl, homopiperidinyl, pyrazolidinyl, imidazolidinyl, piperazinyl, homopiperazinyl, morpholinyl or thiomorpholinyl, and the partially unsaturated derivatives thereof such as e.g. pyrrolinyl, imidazolinyl or pyrazolinyl, and the oxo substituted derivatives of the aforementioned examples such as e.g. 2-oxopyrrolidinyl, 2-oxoimidazolidinyl, 2-oxopiperidinyl, 2,5-dioxopyrrolidinyl, 2,5-dioxoimidazolidinyl, 2,6-dioxopiperidinyl, 2-oxopiperazinyl, or 5-oxo-1,4-diazepanyl, or S-oxo-thiomorpholinyl or S,S-dioxo-thiomorpholinyl, and the benzo-fused derivatives of the aforementioned examples such as e.g. indolinyl, isoindolinyl, 1,2,3,4-tetrahydroquinolinyl or 1,2,3,4-tetrahydroisoquinolinyl, as well as 1,3-benzodioxolyl, 2,3-dihydro-1,4-benzodioxinyl, 2,3-dihydrobenzothiophenyl, chromenyl, chromanyl, or 2,3-dihydrobenzofuranyl.

More detailed exemplary Het radicals include those isomers of the abovementioned examples which are attached via a ring nitrogen atom, such as e.g., without being limited to, aziridin-1-yl, azetidin-1-yl, pyrrolidin-1-yl, piperidin-1-yl, homopiperidin-1-yl, piperazin-1-yl, homopiperazin-1-yl, morpholin-4-yl or thiomorpholin-4-yl, or S-oxo-thiomorpholin-4-yl or S,S-dioxo-thiomorpholin-4-yl.

Yet more detailed exemplary Het radicals include those isomers of the abovementioned examples which are attached via a ring carbon atom, such as e.g., without being limited to, pyrrolidin-2-yl, pyrrolidin-3-yl, piperidin-2-yl, piperidin-3-yl, piperidin-4-yl or piperazin-2-yl.

As used herein, the term "oxo" forms a carbonyl moiety when attached at a carbon atom, a sulfoxide moiety when attached to a sulfur atom and a sulfonyl moiety when two of said terms are attached to a sulfur atom.

Cyc is a group of formula W

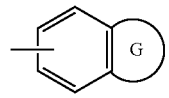

(W)

in which

G is optionally substituted by Rda and/or Rdb on a ring carbon atom, and is a 5- or 6-membered saturated heterocyclic ring comprising one or two heteroatoms independently selected from the group consisting of —N(Rdc)—, oxygen and sulfur, in which Rda is 1-4C-alkyl, or halogen,
Rdb is 1-4C-alkyl, or halogen,
each Rdc is independently selected from the group consisting of: hydrogen, 1-4C-alkyl, and 1-4C-alkylcarbonyl,
whereby said Cyc ring system is attached to the parent molecular group via a substitutable benzoring carbon atom.

As examples of Cyc may be mentioned indolinyl, isoindolinyl, 1,2,3,4-tetrahydroquinolinyl, 1,2,3,4-tetrahydroisoquinolinyl, 1,3-benzodioxolyl, 2,3-dihydro-1,4-benzodioxinyl, 2,3-dihydrobenzothiophenyl, chromanyl or 2,3-dihydrobenzofuranyl.

More detailed exemplary Cyc radicals include, without being limited thereto, 1,3-benzodioxolyl, 2,3-dihydro-1,4-benzodioxinyl, chromanyl or 2,3-dihydrobenzofuranyl, as well as 2,2-difluoro-1,3-benzodioxolyl.

Further more detailed exemplary Cyc radicals include, without being limited thereto, 1,3-benzodioxol-4-yl, 1,3-benzodioxol-5-yl, 2,2-difluoro-1,3-benzodioxol-4-yl, 2,2-difluoro-1,3-benzodioxol-5-yl, 2,3-dihydro-1,4-benzodioxin-5-yl, 2,3-dihydro-1,4-benzodioxin-6-yl, 2,3-dihydrobenzofuran-4-yl, 2,3-dihydrobenzofuran-5-yl, 2,3-dihydrobenzofuran-6-yl or 2,3-dihydrobenzofuran-7-yl.

Illustratively, as an exemplary suitable Cyc radical may be mentioned, without being limited thereto, 2,3-dihydrobenzofuran-6-yl.

It is to be stated that Cyc is an embodiment of Het as defined herein.

In general, unless otherwise mentioned, the terms "Har", "Het" and "Cyc" include all the possible isomeric forms thereof, particularly the positional isomers thereof. Thus, for example, the term pyridyl or pyridinyl includes pyridin-2-yl, pyridin-3-yl and pyridin4-yl.

Unless otherwise noted, constituents which are optionally substituted as stated herein, may be substituted by their substituents or parent molecular groups at any possible position. Notably, unless otherwise mentioned, Ar may be substituted by its substituents or parent molecular groups at any possible position.

Yet notably, unless otherwise mentioned, Har and Het may be substituted by their substituents or parent molecular groups as mentioned herein at any possible position, such as e.g. at any substitutable ring carbon or ring nitrogen atom.

Cyc may be substituted by Rda and/or Rdb at any possible ring carbon atom of the ring G.

Further notable, the moiety Rb of compounds of formula I is attached to the carbonyl portion of the aminocarbonyl group of the scaffold via any possible and allowed position of the Rb ring. Thus e.g., when Rb is Har, the Har moiety is attached to the adjacent carbonyl group at any possible position of the Har ring, particularly the Har moiety is attached to the adjacent carbonyl group at any one of its ring carbon atoms. Likewise, when Rb is Cyc, the Cyc moiety is attached to the adjacent carbonyl group at any possible position of the benzo-moiety of Cyc. Further likewise, when Rb is chromenyl, the chromenyl moiety is attached to the adjacent carbonyl group at any possible position of the chromenyl ring.

Rings containing quaternizable imino-type ring nitrogen atoms (—N=) may be preferably not substituted (i.e. quaternized) on these imino-type ring nitrogen atoms by the mentioned substituents or parent molecular groups.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent.

The person skilled in the art is aware on account of his/her expert knowledge that certain combinations of the variable characteristics mentioned in the description of this invention lead to chemically les stable compounds. This can apply, for example, to certain compounds, in which -in a manner being disadvantageous for chemical stability- two heteroatoms (S, N or O) would directly meet or would only be separated by one carbon atom. This can also apply, for example, to certain free acid derivatives, such as e.g. certain carbamic acid derivatives containing a free carbamic acid function (N—C(O)OH). Those compounds according to this invention, in which the combination of the abovementioned variable substituents does not lead to chemically less stable compounds, are therefore preferred.

Suitable salts for compounds according to this invention - depending on substitution - are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic add, stearic acid, toluenesulphonic acid, methanesulphonic acid or 3-hydroxy-2-naphthoic acid, the acids being employed in salt preparation - depending on whether a mono- or polybasic acid is concerned and depending on which salt is desired - in an equimolar quantitative ratio or one differing therefrom.

On the other hand, salts with bases are - depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to this invention on an industrial scale, are converted into pharmacologically tolerable salts by processes known to the person skilled in the art.

According to experts knowledge the compounds according to this invention as well as their salts may contain, e.g. when isolated in crystalline form, varying amounts of solvents. Included within the scope of the invention are therefore all solvates and in particular all hydrates of the compounds according to this invention as well as all solvates and in particular all hydrates of the salts of the compounds according to this invention.

In the context of this invention, hyperproliferation and analogous terms are used to describe aberrant/dysregulated cellular growth, a hallmark of diseases like cancer. This hyperproliferation might be caused by single or multiple cellular/molecular alterations in respective cells and can be, in context of a whole organism, of benign or malignant behaviour. Inhibition of cell proliferation and analogous terms is used to denote an ability of the compound to retard the growth of and/or kill a cell contacted with that compound as compared to cells not contacted with that compound. Most preferable this inhibition of cell proliferation is 100%, meaning that proliferation of all cells is stopped and/or cells undergo programmed cell death. In some preferred embodiments the contacted cell is a neoplastic cell. A neoplastic cell is defined as a cell with aberrant cell proliferation. A benign neoplasia is described by hyperproliferation of cells, incapable of forming an aggressive, metastasizing tumor in-vivo. In contrast, a malignant neoplasia is described by cells with different cellular and biochemical abnormalities, e.g. capable of forming tumor metastasis. The acquired functional abnormalities of malignant neoplastic cells (also defined as "hallmarks of cancer") are replicative potential ("hyperproliferation"), self-sufficiency in growth signals, insensitivity to anti-growth signals, evasion from apoptosis, sustained angiogenesis and issue invasion and metastasis.

Inducer of apoptosis and analogous terms are used to identify a compound which executes programmed cell death in cells contacted with that compound. Apoptosis is defined by complex biochemical events within the contacted cell, such as the activation of cystein specific proteinases ("caspases") and the fragmentation of chromatin. Induction of apoptosis in cells contacted with the compound might not necessarily coupled with inhibition of cell proliferation. Preferably, the inhibition of cell proliferation and/or induction of apoptosis is specific to cells with aberrant cell growth (hyperproliferation). Thus, compared to cells with aberrant cell growth, normal proliferating or arrested cells are less sensitive or even insensitive to the proliferation inhibiting or apoptosis inducing activity of the compound. Finally, cytotoxic is used in a more general sense to identify compounds which kill cells by various mechanisms, including the induction of apoptosis/programmed cell death in a cell cycle dependent or cell-cycle independent manner.

Cell cycle specific and analogous terms are used to identify a compound as inducing apoptosis only in continuously proliferating cells actively passing a specific phase of the cell cycle, but not in resting, non-dividing cells. Continuously proliferating cells are typical for diseases like cancer and characterized by cells in all phases of the cell division cycle, namely in the G ("gap") 1, S ("DNA synthesis"), G2 and M ("mitosis") phase.

Compounds according to this invention to be mentioned are those compounds of aspect 1, wherein one or where possible more of the following restrictions (these restrictions constitute a group which will be referred to in the following under "restriction group a") apply:

a.) Ra is —C(O)R1, —C(O)OR2, —C(O)SR2, —C(O)N(R3)R4, or —S(O)$_2$R1;
b.) Rb is optionally substituted by Rca and/or Rcb, and is Har, or Cyc, or chromenyl;
c.) R1, R2 and R3 may be the same or different and are independently selected from the group consisting of: 1-7C-alkyl, Ar, or Har, wherein each of said 1-7C-alkyl, Ar and Har can be unsubstituted or optionally substituted by at least one substituent independently selected from R5;
d.) R4 is hydrogen;
e.) each R5, Rca and Rcb may be the same or different and are independently selected from the group consisting of: 1-7C-alkyl, 3-7C-cycloalkyl, Ar, Har, Het, halogen, trifluoromethyl, cyano, nitro, guanidino, amidino, —C(O)R6, —C(O)OR7, —C(O)N(R8)R9, —S(O)$_2$R6, —N(R10)C(O)R6, —N(R10)C(O)N(R8)R9, —OC(O)R6, —OR7, or —N(R8)R(9), wherein each of said 1-7C-alkyl, Ar, Har and Het can be unsubstituted or optionally substituted by at least one substituent independently selected from R11;
f.) R6, R7 and R8 may be the same or different and are independently selected from the group consisting of: hydrogen, 1-7C-alkyl and Ar, wherein each of said 1-7C-alkyl and Ar can be unsubstituted or optionally substituted by at least one substituent independently selected from R12;

g.) each R9 is independently selected from the group consisting of: hydrogen and 1-7C-alkyl;
h.) each R10 is hydrogen;
i.) R11 is selected from the group consisting of: R5 as defined afore for restriction e.);
j.) R12 is selected from the group consisting of: R5 as defined afore for restriction e.);
k.) each Ar is phenyl;
l.) each Har is independently any fully aromatic mono- or fused bicyclic ring or ring system made up of
   a first constituent being a 5- or 6-membered monocyclic unsaturated, aromatic heteroaryl ring A, which heteroaryl ring A comprises one to four heteroatoms independently selected from nitrogen, oxygen and sulfur,
   and, optionally, fused to said first constituent,
   a second constituent being a benzo group, or any additional heteroaryl ring A as defined herein in restriction l.),
   whereby said Har ring or ring system is attached to the parent molecular group via a substitutable ring carbon or ring nitrogen atom;
m.) each Het is independently any fully saturated or partially unsaturated mono- or fused bicyclic ring or ring system made up of
   a first constituent being a 3- or 7-membered monocyclic fully saturated or partially unsaturated, non-aromatic heterocyclic ring B,
      which heterocyclic ring B comprises one to three heteroatoms independently selected from nitrogen, oxygen and sulfur,
      and which heterocyclic ring B is optionally substituted by one or two oxo groups,
   and, optionally, fused to said first constituent,
   a second constituent being a benzo group,
   whereby said Het ring or ring system is attached to the parent molecular group via a substitutable ring carbon or ring nitrogen atom;
n.) Cyc is as defined in aspect 1 above;

and the salts, solvates or the solvates of the salts thereof.

Compounds according to this invention further to be mentioned are those compounds of aspect 1, wherein one or, particularly, where possible more of the following restrictions (these restrictions constitute a group which will be referred to in the following under "restriction group b") apply:

a.) Ra is —C(O)R1;
b.) Ra is —C(O)OR2;
c.) Ra is —C(O)SR2;
d.) Rb is optionally substituted by Rca and/or Rcb, and is Har, in which either
   Har is a 5-membered monocyclic unsaturated, aromatic heteroaryl radical comprising one to four heteroatoms independently selected from oxygen, nitrogen and sulfur, or
   Har is a 6-membered monocyclic unsaturated, aromatic heteroaryl radical comprising one or two nitrogen atoms, or
   Har contains optionally a benzene ring moiety, and is a 10-membered fused bicyclic unsaturated, aromatic heteroaryl radical comprising one to four heteroatoms independently selected from oxygen, nitrogen and sulfur, or
   Har contains optionally a benzene ring moiety, and is a 11-membered fused bicyclic unsaturated, aromatic heteroaryl radical comprising one to four heteroatoms independently selected from oxygen, nitrogen and sulfur,
   whereby said Har ring or ring system is attached to the parent molecular group via a substitutable ring carbon atom;

e.) Rb is Cyc, in which
Cyc is of formula W as defined above, in which
G is optionally substituted by Rda and/or Rdb on a ring carbon atom, and is a 5- or 6-membered saturated heterocyclic ring comprising one or two heteroatoms independently selected from the group consisting of —N(Rdc)—, oxygen and sulfur, in which
Rda is 1-4-C-alkyl, or fluorine,
Rdb is 1-4-C-alkyl, or fluorine,
each Rdc is independently selected from the group consisting of: hydrogen, 1-4C-alkyl, and 1-4C-alkylcarbonyl,
whereby said Cyc ring system is attached to the parent molecular group via a substitutable benzoring carbon atom;
f.) Rb is chromenyl;
g.) R1 and R2 may be the same or different and are independently selected from the group consisting of: 1-7C-alkyl, or 1-7C-alkyl substituted by at least one substituent selected from R5;
h.) R5, Rca and Rcb may be the same or different and are independently selected from the group consisting of:
1-7C-alkyl, 3-7C-cycloalkyl, Ar, Har, Het, halogen, trifluoromethyl, cyano, nitro, guanidino, amidino, —C(O)R6, —C(O)OR7, —C(O)N(R8)R9, —S(O)$_2$R6, —N(R10)C(O)R6, —N(R10)C(O)N(R8)R9, —OC(O)R6, —OR7, or —N(R8)R(9), wherein each of said 1-7C-alkyl, Ar, Har and Het can be unsubstituted or optionally substituted by at least one substituent independently selected from R11;
i.) R6, R7 and R8 may be the same or different and are independently selected from the group consisting of: hydrogen, 1-7C-alkyl and Ar, wherein each of said 1-7C-alkyl and Ar can be unsubstituted or optionally substituted by at least one substituent independently selected from R12;
j.) each R9 is independently selected from the group consisting of: hydrogen and 1-7C-alkyl;
k.) each R10 is hydrogen;
l.) R11 is selected from the group consisting of: R5 as defined afore for restriction h.);
m.) R12 is selected from the group consisting of: R5 as defined afore for restriction h.);
n.) each Ar is phenyl;
o.) except for restriction d.) afore, each Har is independently any fully aromatic mono- or fused bicyclic ring or ring system made up of
a first constituent being a 5- or 6-membered monocyclic unsaturated, aromatic heteroaryl ring A, which heteroaryl ring A comprises one to four heteroatoms independently selected from nitrogen, oxygen and sulfur,
and, optionally, fused to said first constituent,
a second constituent being a benzo group, or any additional heteroaryl ring A as defined in this restriction o.),
whereby said Har ring or ring system is attached to the parent molecular group via a substitutable ring carbon or ring nitrogen atom;
p.) each Het is independently any fully saturated or partially unsaturated mono- or fused bicyclic ring or ring system made up of
a first constituent being a 3- or 7-membered monocyclic fully saturated or partially unsaturated, non-aromatic heterocyclic ring B,
which heterocyclic ring B comprises one to three heteroatoms independently selected from nitrogen, oxygen and sulfur,
and which heterocyclic ring B is optionally substituted by one or two oxo groups,
and, optionally, fused to said first constituent,
a second constituent being a benzo group,
whereby said Het ring or ring system is attached to the parent molecular group via a substitutable ring carbon or ring nitrogen atom, and the salts, solvates or the solvates of the salts thereof.

Compounds according to this invention also further to be mentioned are those compounds of formula I, in which, in a first alternative,
Ra is —C(O)R1, in which,
R1 is 1-7C-alkyl, or in which, in a second alternative,
Ra is —C(O)OR2, in which,
R2 is 1-7C-alkyl, or in which, in a third alternative,
Ra is —C(O)SR2, in which,
R2 is 1-7C-alkyl, or in which, in a fourth alternative,
Ra is —C(O)R1, in which,
R1 is substituted by R5, and is 1-4C-alkyl, especially ethyl or propyl, in which either
R5 is 1-4C-alkoxycarbonyl, 1-4C-alkylcarbonyl, carbamoyl, or 1-4C-alkoxy, or
R5 is indolyl, or thiophenyl, or in which, in a fifth alternative,
Ra is —C(O)OR2, in which,
R2 is substituted by R5, and is 2-4C-alkyl, especially ethyl, in which either
R5 is 1-4C-alkoxy, or
R5 is 4methyl-thiazol-5-yl, whereby in particular
Ra is ethoxycarbonyl;

and in which
Rb is 3-methyl-5-phenyl-isoxazol-4-yl, 3-phenyl-5-methyl-isoxazol4-yl, or thiophenyl, such as e.g. thiophen-2-yl, or benzothiophenyl, such as e.g. benzothiophen-2-yl, or benzofuranyl, such as e.g. benzofuran-5-yl, or pyridyl, such as e.g. pyridin-3-yl, or pyrazinyl, such as e.g. pyrazin-2-yl, or thiophenyl substituted by 1-4C-alkyl, such as e.g. 5-methyl-thiophen-2-yl, or 1,3-benzodioxolyl, such as e.g. 1,3-benzodioxol-5-yl, or 2,3-dihydro-1,4-benzodioxinyl, such as e.g. 2,3-dihydro-1,4-benzodioxin-5-yl, or chromenyl, such as e.g. chromen-3-yl, whereby in particular
Rb is 5-methyl-thiophen-2-yl, pyridin-3-yl, or benzofuran-5-yl;

and the salts, solvates or the solvates of the salts thereof.

Compounds according to aspect I of this invention more worthy to be mentioned are those compounds of formula I, in which
Ra is —C(O)R1, in which either
R1 is 1-6C-alkyl, or
R1 is 1-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, amino, morpholino, piperidino, pyrrolidino, 4N-(1-4C-alkyl)-piperazino, mono- or di-1-4C-alkylamino, mono- or di-1-4-C-alkylaminocarbonyl, carbamoyl, ureido, guanidino, imidazolo, triazolo, pyrazolo, 1-4C-alkylcarbonyloxy or 1-4C-alkylcarbonylamino,
   wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, imidazolo, pyrazolo or phenyl radicals alone or part of another group may be unsubstituted or optionally substituted by one or two substituents independently selected from halogen, 1-4C-alkoxy, nitro and 1-4C-alkyl, or
R1 is 3-4C-alkyl which is substituted by two hydroxyl groups on different carbon atoms, or
R1 is 1-2C-alkyl which is substituted by 2,2-dimethyl-[1,3]dioxolan-4-yl;

or in which
Ra is —C(O)OR2, in which either
R2 is 1-6C-alkyl, or
R2 is 1-4C-alkyl which is mono-substituted by R5, in which
R5 is pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, mono- or di-1-4C-alkylaminocarbonyl or carbamoyl, wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl or phenyl radicals can be unsubstituted or optionally substituted by one or two substituents independently selected from halogen, 1-4C-alkoxy, nitro and 1-4C-alkyl, or
R2 is 2-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkylcarbonylamino, wherein each of said imidazolo, pyrazolo or phenyl radicals alone or part of another group can be unsubstituted or optionally substituted by one or two substituents independently selected from halogen, 1-4C-alkoxy, nitro and 1-4C-alkyl, or
R2 is 3-4C-alkyl which is substituted by two hydroxyl groups on different carbon atoms, or
R2 is 1-2C-alkyl which is substituted by 2,2-dimethyl-[1,3]dioxolan-4-yl;

or in which
Ra is —C(O)SR2, in which either
R2 is 1-6C-alkyl, or
R2 is 1-4C-alkyl which is mono-substituted by R5, in which
R5 is pyridyl, pyrimidinyl, pyrazinyl, indolyl, benzofuranyl, benzothiophenyl, thiazolyl, oxazolyl, 1N-(1-4C-alkyl)-imidazolyl, 1N-(1,4C-alkyl)-pyrazolyl, phenyl, 1-4C-alkoxycarbonyl, carboxyl, mono- or di-1-4C-alkylaminocarbonyl or carbamoyl,
   wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl or phenyl radicals can be unsubstituted or optionally substituted by one or two substituents independently selected from halogen, 1-4C-alkoxy, nitro and 1-4C-alkyl, or
R2 is 2-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkylcarbonylamino,
   wherein each of said imidazolo, pyrazolo or phenyl radicals alone or part of another group can be unsubstituted or optionally substituted by one or two substituents independently selected from halogen, 1-4C-alkoxy, nitro and 1-4C-alkyl;

and in which either
Rb is optionally substituted by Rca and/or Rcb, and is Har, or
Rb is Cyc, or
   Rb is chromenyl, in which
Har is either
   a 5-membered monocyclic heteroaryl radical comprising one, two or three heteroatoms independently selected from nitrogen, oxygen and sulphur, such as e.g. any one selected from furanyl, thiophenyl, pyrrolyl, oxazolyl, isoxazolyl, thiazolyl, isothiazolyl, imidazolyl, pyrazolyl, triazolyl, thiadiazolyl and oxadiazolyl, or
   a 6-membered monocyclic heteroaryl radical comprising one or two nitrogen atoms, such as e.g. any one selected from pyridinyl, pyrazinyl, pyridazinyl and pyrimidinyl, or
   a 9-membered fused bicyclic heteroaryl radical comprising one, two or three heteroatoms independently selected from nitrogen, oxygen and sulphur, such as e.g. any one selected from indolyl, benzothiophenyl, benzofuranyl, benzoxazoly, benzisoxazolyl, benzothiazolyl, benzoisothiazolyl, benzimidazolyl, indazolyl, benzotriazolyl, benzothiadiazolyl and benzoxadiazolyl, or
   a 10-membered fused bicyclic heteroaryl radical comprising one, two or three heteroatoms independently selected from nitrogen, oxygen and sulphur, such as e.g. any one selected from quinolinyl, isoquinolinyl, quinoxalinyl, quinazolinyl and cinnolinyl, whereby said Har radical is attached to the parent molecular group via a ring carbon atom,
Cyc is 1,3-benzodioxolyl, 2,3-dihydro-1,4-benzodioxinyl, 2,2-difluoro-1,3-benzodioxolyl, 2,2-dimethyl-1,3-benzodioxolyl, chromanyl or 2,3-dihydro-benzofuranyl, whereby said Cyc ring system is attached to the parent molecular group via a substitutable benzoring carbon atom,
Rca is halogen, 1-4C-alkyl, 1-4C-alkoxy, phenyl, phenoxy or morpholino,
Rcb is halogen, 1-4C-alkyl or 1-4C-alkoxy;

and the salts, solvates or the solvates of the salts thereof.
Compounds according to aspect 1 of this invention in particular worthy to be mentioned are those compounds of formula I, in which
Ra is —C(O)R1, in which either
R1 is methyl, ethyl, propyl or butyl, or
R1 is methyl which is mono-substituted by R5, ethyl which is mono-substituted by R5, or propyl which is mono-substituted by R5, in which
R5 is methoxy, ethoxy, 2-methoxyethoxy, 2-(2-methoxyethoxy)-ethoxy, hydroxyl, pyridyl, pyrimidinyl, pyrazinyl, indolyl, thiazolyl, oxazolyl, 1N-methyl-imidazolyl, 1N-methyl-pyrazolyl, phenyl, methoxycarbonyl, ethoxycarbonyl, carboxyl, dimethylaminocarbonyl, morpholino, carbamoyl, ureido, guanidino, imidazolo, triazolo, pyrazolo, ethylcarbonyloxy or methylcarbonyloxy, or R1 is propyl or butyl, each of which is substituted by two hydroxyl groups on different carbon atoms, or R1 is methyl or ethyl, each of which is substituted by 2,2-dimethyl-[1,3]dioxolan-4-yl;

or in which

Ra is —C(O)OR2, in which either

R2 is methyl, ethyl, propyl or butyl, or

R2 is cyclohexyl, phenyl, pyridyl, (1-2C-alkoxycarbonyl)-phenyl, or (1-2C-alkoxy)-phenyl, or R2 is methyl which is mono-substituted by R5, ethyl which is mono-substituted by R5, or propyl which is mono-substituted by R5, in which R5 is pyridyl, pyrimidinyl, pyrazinyl, 1N-methyl-imidazolyl, 1N-methyl-pyrazolyl, phenyl, (1-2C-alkoxy)-phenyl, methoxycarbonyl, ethoxycarbonyl, carboxyl, di-methylaminocarbonyl or carbamoyl, or R2 is ethyl which is mono-substituted by R5, or propyl which is mono-substituted by R5, in which R5 is methoxy, ethoxy, 2-methoxyethoxy, 2-(2-methoxyethoxy)-ethoxy, hydroxyl, benzyloxy, phenoxy, morpholino, piperidino, pyrrolidino, 4N-(methyl)-piperazino, dimethylamino, imidazolo, triazolo, pyrazolo, methylcarbonyloxy, ethylcarbonyloxy, methylcarbonylamino or ethylcarbonylamino, or R2 is propyl or butyl, each of which is substituted by two hydroxyl groups on different carbon atoms, or R2 is methyl or ethyl, each of which is substituted by 2,2-dimethyl-[1,3]dioxolan-4-yl;

or in which

Ra is —C(O)SR2, in which either

R2 is methyl, ethyl, propyl, butyl or pentyl, or

R2 is methyl which is mono-substituted by R5, ethyl which is mono-substituted by R5, or propyl which is mono-substituted by R5, in which R5 is pyridyl, or R2 is ethyl which is mono-substituted by R5, or propyl which is mono-substituted by R5, in which R5 is hydroxyl, methoxy or ethoxy;

and in which either

Rb is substituted by Rca, and is thiophenyl, furanyl, pyridyl or (phenyl)-isoxazolyl, or Rb is unsubstituted, and is thiophenyl, furanyl, pyridyl, benzofuranyl or benzothiophenyl, or Rb is 1,3-benzodioxol-5-yl, 1,3-benzodioxol-4-yl, 2,2-difluoro-1,3-benzodioxol-5-yl, 2,2-difluoro-1,3-benzodioxol-6-yl, 2,3-dihydro-1,4-benzodioxin-5-yl, 2,3-dihydro-1,4-benzodioxin-6-yl, 2,3-dihydro-benzofuran-4-yl, 2,3-dihydro-benzofuran-5-yl, 2,3-dihydro-benzofuran-6-yl or 2,3-dihydro-benzofuran-7-yl, or Rb is chromenyl, in which Rca is methyl or ethyl;

and the salts, solvates or the solvates of the salts thereof.

Compounds according to aspect 1 of this invention in more particular worthy to be mentioned are those compounds of formula I, in which Ra is —C(O)R1, in which either R1 is methyl, ethyl or propyl, or R1 is (R5)-methyl, 2-(R5)-ethyl, or 3-(R5)-propyl, in which R5 is methoxy, ethoxy, 2-methoxyethoxy, 2-(2-methoxyethoxy)-ethoxy, hydroxyl, pyridyl, pyrimidinyl, pyrazinyl, imidazolo, pyrazolo or methylcarbonyloxy, or R1 is 2,3-dihydroxy-propyl;

or in which

Ra is —C(O)OR2, in which either

R2 is methyl, ethyl or propyl, or

R2 is (R5)-methyl, 2-(R5)-ethyl, or 3-(R5)-propyl, in which

R5 is pyridyl, pyrazinyl or pyrimidinyl, or

R2 is 2-(R5)-ethyl, or 3-(R5)-propyl, in which

R5 is methoxy, ethoxy, 2-methoxyethoxy, 2-(2-methoxyethoxy)-ethoxy, hydroxyl, imidazolo, pyrazolo or methylcarbonyloxy, or R2 is 2,3-dihydroxy-propyl;

or in which

Ra is —C(O)SR2, in which either

R2 is methyl, ethyl or propyl, or

R2 is (R5)-methyl, 2-(R5)-ethyl, or 3-(R5)-propyl, in which

R5 is pyridyl, or

R2 is 2-(R5)-ethyl, or 3-(R5)-propyl, in which

R5 is hydroxyl;

and in which either

Rb is substituted by Rca, and is thiophenyl or furanyl, or

Rb is unsubstituted, and is thiophenyl, furanyl, pyridyl, benzofuran-4-yl, benzofuran-5-yl, benzofuran-6-yl or benzofuran-7-yl, or Rb is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,3-dihydro-benzofuran-4-yl, 2,3-dihydro-benzofuran-5-yl, 2,3-dihydro-benzofuran-6-yl or 2,3-dihydro-benzofuran-7-yl, in which Rca is methyl;

and the salts, solvates or the solvates of the salts thereof.

Compounds according to aspect 1 of this invention to be emphasized are those compounds of formula I, in which Ra is —C(O)OR2, in which R2 is ethyl, or in which Ra is —C(O)SR2, in which R2 is ethyl;

and in which either

Rb is substituted by methyl, and is thiophen-2-yl or thiophen-3-yl, particularly 5-methyl-thiophen-2-yl, or Rb is pyridin-2-yl, pyridin-3-yl, pyridin4-yl, benzofuran4-yl, benzofuran-5-yl, benzofuran-6-yl or benzofuran-7-yl, particularly pyridin-3-yl or benzofuran-6-yl, or Rb is 2,3-dihydro-benzofuran-4-yl, 2,3-dihydro-benzofuran-5-yl, 2,3-dihydro-benzofuran-6-yl or 2,3-dihydro-benzofuran-7-yl, particularly 2,3-dihydro-benzofuran-6-yl;

and the salts, solvates or the solvates of the salts thereof.

In the compounds according to the present invention, the significances mentioned in the following details/subdetails and/or variants/subvariants are of concern individually or in any combination thereof:

A first detail (detail a) of the compounds according to this invention includes those compounds of formula I, in which Ra is —C(O)R1.

A subdetail (detail a1) of the compounds according to detail a of this invention include those compounds of formula I, in which Ra is —C(O)R1, in which R1 is hydrogen, 1-7C-alkyl, 3-7C-cycloalkyl, or 1-7C-alkyl substituted by any of R5 as defined in aspect 1 above, or, in an embodimental alternative, 1-7C-alkyl substituted by any of R5 as defined in restriction e (according to restriction group a) or in restriction h (according to restriction group b) above.

A more precise subdetail (detail a11) of the compounds according to detail a of this invention include those compounds of formula I, in which Ra is —C(O)R1, in which R1 is 1-7C-alkyl, or 1-7C-alkyl substituted by R5, in which R5 is 1-4C-alkoxycarbonyl, 1-4C-alkylcarbonyl, carbamoyl, guanidino, amidino, carboxyl, mono- or di-1-4C-alkylaminocarbonyl, mono- or di-1-4C-alkylamino, ureido, 1-4C-alkoxy, hydroxyl, 1-4C-alkoxy-2-4C-alkoxy, or phenyl-1-4C-alkoxy;

in an interesting embodiment thereof

R1 is 1-4C-alkyl substituted by R5, in which

R5 is 1-2C-alkoxycarbonyl, acetyl, guanidino, carbamoyl, carboxyl, dimethylaminocarbonyl, dimethylamino, ureido, methoxy, hydroxyl, or 2-methoxyethoxy;

in a more interesting embodiment thereof

R1 is 1-4C-alkyl, especially ethyl or propyl, substituted by R5, in which

R5 is carbamoyl, methoxy, methoxycarbonyl, or acetyl.

Another more precise subdetail (detail a12) of the compounds according to detail a of this invention include those compounds of formula I, in which Ra is —C(O)R1, in which R1 is 1-7C-alkyl, or 1-7C-alkyl substituted by R5, in which either R5 is phenyl, or R51-substituted phenyl, in which R51 is 1-4C-alkoxy, or R5 is Har, R52-substituted Har, or Het, in which, in a first alternative thereof, Har is attached to the parent molecular group via any ring carbon or ring nitrogen atom, and is an unsaturated (aromatic) 5-membered ring comprising one to four heteroatoms independently selected from nitrogen, oxygen and sulfur which is optionally fused to a benzene ring, or, in a second alternative thereof, Har is attached to the parent molecular group via any ring carbon atom, and is an unsaturated (aromatic) 6-membered ring comprising one or two nitrogen atoms independently selected from nitrogen, oxygen and sulfur which is optionally fused to a benzene ring, R52 is 1-4-C-alkyl, or, in a third alternative thereof, Het is attached to the parent molecular group via any ring nitrogen atom, and is a saturated 3- to 7-membered monocyclic ring comprising one or two heteroatoms independently selected from nitrogen, —N(R53)-, oxygen and sulfur, and which is optionally substituted by one or two oxo groups, or a benzo-fused derivative thereof, in which R53 is 1-4-C-alkyl, or 1-4C-alkylcarbonyl, or, in a fourth alternative thereof, Het is attached to the parent molecular group via any ring carbon atom, and is a saturated 3- to 7-membered monocyclic ring comprising one or two heteroatoms independently selected from nitrogen, —N(R53)—, oxygen and sulfur, which is optionally substituted by one or two oxo groups, and which is optionally fused to a benzene ring, in which R53 is 1-4C-alkyl, or 1-4C-alkylcarbonyl;

in an interesting embodiment thereof

R1 is 1-4C-alkyl substituted by R5, in which

R5 is Har, or Het, in which, in said first alternative,

Har is indolyl, thiophenyl, N-methyl-imidazolyl, methyl-thiazolyl, or imidazolyl (such as e.g. indol-2-yl, indol-3-yl, thiophen-2-yl, 4-methyl-thiazol-5-yl, 1-N-methyl-imidazol-5-yl, 1-N-methyl-imidazol-4-yl, 1-NH-imidazol-4-yl, or imidazol-1-yl), or, in said second alternative, Har is pyridyl, or pyrazinyl (such as e.g. pyridin-2-yl, pyridin-3-yl, or pyridin-4-yl, or pyrazin-2-yl), or, in said third alternative, Het is piperidinyl, morpholinyl, N-methyl-piperazinyl, or pyrrolidinyl (such as e.g. piperidin-1-yl, morpholino, 4N-methyl-piperazin-1-yl, or pyrrolidino-1-yl), or, in said fourth alternative, Het is 1,3-benzodioxolyl (such as e.g. 1,3-benzodioxol-5-yl);

in a more interesting embodiment thereof

R1 is 1-4C-alkyl, especially ethyl or propyl, substituted by R5, in which

R5 is Har, in which

Har is indolyl (such as e.g. indol-2-yl), thiophenyl (such as e.g. thiophen-2-yl), or methyl-thiazolyl (such as e.g. 4-methyl-thiazol-5-yl).

Another more precise subdetail (detail a13) of the compounds according to detail a of this invention include those compounds of formula I, in which Ra is —C(O)R1, in which R1 is 1-7C-alkyl, 3-7C-cycloalkyl, or 3-7C-cycloalkyl-1-4C-alkyl;

in an interesting embodiment thereof

R1 is 1-7C-alkyl;

in a more interesting embodiment thereof

R1 is methyl, propyl, or hexyl.

A notable subdetail (detail a14) of the compounds according to detail a of this invention include those compounds of formula I, in which Ra is —C(O)R1, in which R1 is methyl, ethyl, propyl or butyl.

Another notable subdetail (detail a15) of the compounds according to detail a of this invention include those compounds of formula I, which Ra is —C(O)R1, in which R1 is (R5)-methyl, 2-(R5)-ethyl, or 3-(R5)-propyl, in which R5 is pyridyl, pyrimidinyl, pyrazinyl, imidazolo or pyrazolo.

Another notable subdetail (detail a16) of the compounds according to detail a of this invention include those compounds of formula I, in which Ra is —C(O)R1, in which R1 is (R5)-methyl, 2-(R5)-ethyl, or 3-(R5)-propyl, in which R5 is methoxy, ethoxy, 2-methoxyethoxy, 2-(2-methoxyethoxy)ethoxy, hydroxyl or methylcarbonyloxy.

A more notable subdetail (detail a17) of the compounds according to detail a of this invention include those compounds of formula I, in which Ra is —C(O)R1, in which R1 is any one selected from methyl, ethyl and propyl.

Another more notable subdetail (detail a18) of the compounds according to detail a of this invention include those compounds of formula I, in which Ra is —C(O)R1, in which R1 is any one selected from methoxy-methyl, 2-methoxy-ethyl, (2-methoxyethoxy)-methyl, 2-(2-methoxyethoxy)-ethyl, hydroxy-methyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl and 2-(pyridin-4-yl)-ethyl.

Another more notable subdetail (detail a19) of the compounds according to detail a of this invention include those compounds of formula I, in which Ra is —C(O)R1, in which R1 is 2,3-dihydroxypropyl.

A second detail (detail b) of the compounds according to this invention includes those compounds of formula I, in which Ra is —C(O)OR2.

A subdetail (detail bi) of the compounds according to detail b of this invention include those compounds of formula I, in which Ra is —C(O)OR2, in which R2 is 1-7C-alkyl, or 3-7C-cycloalkyl, or 1-7C-alkyl substituted by any of R5 as defined in aspect 1 above, or, in an embodimental alternative, 1-7C-alkyl substituted by any of R5 as defined in restriction e (according to restriction group a) or in restriction h (according to restriction group b) above.

A more precise subdetail (detail b11) of the compounds according to detail b of this invention include those compounds of formula I, in which Ra is —C(O)OR2, in which R2 is 1-7C-alkyl, or 1-7C-alkyl substituted by R5, in which R5 is 1-4C-alkoxycarbonyl, 1-4C-alkylcarbonyl, carbamoyl, guanidino, amidino, carboxyl, mono- or di-1-4C-alkylaminocarbonyl, mono- or di-1-4C-alkylamino, ureido, 1-4C-alkoxy, hydroxyl, 1-4C-alkoxy-2-4C-alkoxy, or phenyl-1-4C-alkoxy;

in an interesting embodiment thereof

R1 is 1-4C-alkyl substituted by R5, in which

R5 is 1-2C-alkoxycarbonyl, carboxyl, dimethylaminocarbonyl, dimethylamino, methoxy, hydroxyl, or 2-methoxyethoxy;

in a more interesting embodiment thereof

R1 is ethyl substituted by R5, in which

R5 is methoxy.

Another more precise subdetail (detail b12) of the compounds according to detail b of this invention include those compounds of formula I, in which Ra is —C(O)OR2, in which R2 is 1-7C-alkyl, or 1-7C-alkyl substituted by R5, in which either R5 is phenyl, or R51-substituted phenyl, in which R51 is 1-4C-alkoxy, or R5 is Har, R52-substituted Har, or Het, in which, in a first alternative thereof, Har is attached to the parent molecular group via any ring carbon or ring nitrogen atom, and is an unsaturated (aromatic) 5-membered ring comprising one to four heteroatoms independently selected from nitrogen, oxygen and sulfur which is optionally fused to a benzene ring, or, in a second alternative thereof, Har is attached to the parent molecular group via any ring carbon atom, and is an unsaturated (aromatic) 6-membered ring comprising one or two nitrogen atoms independently selected from nitrogen, oxygen and sulfur which is optionally fused to a benzene ring, R52 is 1-4C-alkyl, or, in a third alternative thereof, Het is attached to the parent molecular group via any ring nitrogen atom, and is a saturated 3- to 7-membered monocyclic ring comprising one or two heteroatoms independently selected from nitrogen, —N(R53)—, oxygen and sulfur, and which is optionally substituted by one or two oxo groups, or a benzo-fused derivative thereof, in which R53 is 1-4C-alkyl, or 1-4C-alkylcarbonyl, or, in a fourth alternative thereof, Het is attached to the parent molecular group via any ring carbon atom, and is a saturated 3- to 7-membered monocyclic ring comprising one or two heteroatoms independently selected from nitrogen, —N(R53)—, oxygen and sulfur, which is optionally substituted by one or two oxo groups, and which is optionally fused to a benzene ring, in which R53 is 1-4C-alkyl, or 1-4C-alkylcarbonyl;

in an interesting embodiment thereof

R1 is 1-4C-alkyl substituted by R5, in which

R5 is Har, or Het, in which, in said first alternative,

Har is indolyl, thiophenyl, N-methyl-imidazolyl, methyl-thiazolyl, or imidazolyl (such as e.g. indol-2-yl, indol-3-yl, thiophen-2-yl, 4-methyl-thiazol-5-yl, 1-N-methyl-imidazol-5-yl, 1-N-methyl-imidazol4-yl, 1-NH-imidazol-4-yl, or imidazol-1-yl), or, in said second alternative, Har is pyridyl, or pyrazinyl (such as e.g. pyridin-2-yl, pyridin-3-yl, or pyridin-4-yl, or pyrazin-2-yl), or, in said third alternative, Het is piperidinyl, morpholinyl, N-methyl-piperazinyl, or pyrrolidinyl (such as e.g. piperidin-1-yl, morpholino, 4N-methyl-piperazin-1-yl, or pyrrolidino-1-yl), or, in said fourth alternative, Het is 1,3-benzodioxolyl (such as e.g. 1,3-benzodioxol-5-yl);

in a more interesting embodiment thereof

R1 is ethyl substituted by R5, in which

R5 is Har, in which

Har is methyl-thiazolyl (such as e.g. 4-methyl-thiazol-5-yl).

Another more precise subdetail (detail b13) of the compounds according to detail b of this invention include those compounds of formula I, in which Ra is —C(O)OR2, in which R2 is 1-7C-alkyl, 3-7C-cycloalkyl, or 3-7C-cycloalkyl-1-4C-alkyl;

in an interesting embodiment thereof

R2 is 1-7C-alkyl;

in a more interesting embodiment thereof

R2 is methyl, ethyl, tertbutyl, or pentyl, particularly ethyl.

A notable subdetail (detail b14) of the compounds according to detail b of this invention include those compounds of formula I, in which in which Ra is —C(O)OR2, in which R2 is methyl, ethyl, propyl or butyl.

Another notable subdetail (detail b15) of the compounds according to detail b of this invention include those compounds of formula I, in which
Ra is —C(O)OR2, in which
R2 is (R5)-methyl, 2-(R5)-ethyl, or 3-(R5)-propyl, in which
R5 is pyridyl, pyrimidinyl or pyrazinyl.

Another notable subdetail (detail b16) of the compounds according to detail b of this invention include those compounds of formula I, in which
Ra is —C(O)OR2, in which
R2 is 2-(R5)-ethyl, or 3-(R5)-propyl, in which
R5 is methoxy, ethoxy, 2-methoxyethoxy, 2-(2-methoxyethoxy)ethoxy, hydroxyl or methylcarbonyloxy.

A more notable subdetail (detail b17) of the compounds according to detail b of this invention include those compounds of formula I, in which
Ra is —C(O)OR2, in which
R2 is any one selected from methyl, ethyl and propyl.

Another more notable subdetail (detail b18) of the compounds according to detail b of this invention include those compounds of formula I, in which
Ra is —C(O)OR2, in which
R2 is any one selected from 2-methoxy-ethyl, 2-(2-methoxy-ethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl and 2-(pyridin-4-yl)-ethyl.

Another more notable subdetail (detail b19) of the compounds according to detail b of this invention include those compounds of formula I, in which
Ra is —C(O)OR2, in which
R2 is 2,3-dihydroxypropyl.

A third detail (detail c) of the compounds according to this invention includes those compounds of formula I, in which
Ra is —C(O)SR2.

A notable subdetail (detail c1) of the compounds according to detail c of this invention include those compounds of formula I, in which in which
Ra is —C(O)SR2, in which
R2 is methyl, ethyl, propyl or butyl.

Another notable subdetail (detail c2) of the compounds according to detail c of this invention include those compounds of formula I, in which
Ra is —C(O)SR2, in which
R2 is (R5)-methyl, 2-(R5)-ethyl, or 3-(R5)-propyl, in which
R5 is pyridyl, pyrimidinyl or pyrazinyl.

Another notable subdetail (detail c3) of the compounds according to detail c of this invention include those compounds of formula I, in which
Ra is —C(O)SR2, in which
R2 is 2-(R5)-ethyl, or 3-(R5)-propyl, in which
R5 is methoxy, ethoxy, 2-methoxyethoxy, 2-(2-methoxyethoxy)ethoxy, hydroxyl or methylcarbonyloxy.

A more notable subdetail (detail c4) of the compounds according to detail c of this invention include those compounds of formula I, in which
Ra is —C(O)SR2, in which
R2 is any one selected from methyl, ethyl and propyl.

Another more notable subdetail (detail c5) of the compounds according to detail c of this invention include those compounds of formula I, in which
Ra is —C(O)SR2, in which
R2 is any one selected from 2-methoxy-ethyl, 2-(2-methoxy-ethoxy)-ethyl, 2-hydroxy-ethyl, (pyridin-2-yl)-methyl, (pyridin-3-yl)-methyl, (pyridin-4-yl)-methyl, 2-(pyridin-2-yl)-ethyl, 2-(pyridin-3-yl)-ethyl and 2-(pyridin-4-yl)-ethyl.

A first variant (variant a) of the compounds according to this invention includes those compounds of formula I, in which
Rb is optionally substituted by Rca and/or Rcb, and is Har.

A subvariant (variant a1) of the compounds according to variant a of this invention includes those compounds of formula I, in which
Rb is optionally substituted by Rca and/or Rcb, and is Har, in which either
Har is a 5-membered monocyclic unsaturated, aromatic heteroaryl radical comprising one to four heteroatoms independently selected from oxygen, nitrogen and sulfur, or
Har is a 6-membered monocyclic unsaturated, aromatic heteroaryl radical comprising one or two nitrogen atoms, or
Har contains optionally a benzene ring moiety, and is a 10-membered fused bicyclic unsaturated, aromatic heteroaryl radical comprising one to four heteroatoms independently selected from oxygen, nitrogen and sulfur, or
Har contains optionally a benzene ring moiety, and is a 11-membered fused bicyclic unsaturated, aromatic heteroaryl radical comprising one to four heteroatoms independently selected from oxygen, nitrogen and sulfur,
whereby said Har ring or ring system is attached to the parent molecular group via a substitutable ring carbon atom;

and in which
Rca and Rcb are independently as defined in aspect 1 above, or,
in an embodimental alternative,
Rca and Rcb are independently as defined in restriction e (according to restriction group a) or in restriction h (according to restriction group b) above.

A more precise subvariant (variant a11) of the compounds according to variant a of this invention includes those compounds of formula I, in which
Rb is optionally substituted by Rca and/or Rcb, and is Har, in which either
Har is a 5-membered monocyclic unsaturated, aromatic heteroaryl radical comprising one to four heteroatoms independently selected from oxygen, nitrogen and sulfur, or
Har is a 6-membered monocyclic unsaturated, aromatic heteroaryl radical comprising one or two nitrogen atoms, or
Har contains optionally a benzene ring moiety, and is a 10-membered fused bicyclic unsaturated, aromatic heteroaryl radical comprising one to four heteroatoms independently selected from oxygen, nitrogen and sulfur, or Har contains optionally a benzene ring moiety, and is a 11-membered fused bicyclic unsaturated, aromatic heteroaryl radical comprising one to four heteroatoms independently selected from oxygen, nitrogen and sulfur, whereby said Har ring or ring system is attached to the parent molecular group via a substitutable ring carbon atom;

and in which

Rca is 1-4C-alkyl, halogen, phenyl, nitro, or phenylsulfonyl,

Rcb is 1-4C-alkyl, or halogen.

A further more precise subvariant (variant a12) of the compounds according to variant a of this invention includes those compounds of formula I, in which Rb is optionally substituted by Rca and/or Rcb, and is Har, in which either Har is thiophenyl, isoxazolyl, or oxazolyl, or Har is pyridyl, or pyrazinyl, or Har is indolyl, benzothiophenyl, or benzofuranyl, whereby said Har ring or ring system is attached to the parent molecular group via a substitutable ring carbon atom;

and in which

Rca and Rcb are independently as defined in aspect 1 above, or, in an embodimental alternative Rca and Rcb are independently as defined in restriction e (according to restriction group a) or in restriction h (according to restriction group b) above.

A yet further more precise subvariant (variant a13) of the compounds according to variant a of this invention includes those compounds of formula I, in which Rb is optionally substituted by Rca and/or Rcb, and is Har, in which either Har is thiophenyl, isoxazolyl, or oxazolyl, or Har is pyridyl, or Har is indolyl, benzothiophenyl, or benzofuranyl, whereby said Har ring or ring system is attached to the parent molecular group via a substitutable ring carbon atom;

and in which

Rca is 1-4C-alkyl, halogen, phenyl, nitro, or phenylsulfonyl,

Rcb is 1-4C-alkyl, or halogen;

in an interesting embodiment thereof

Rb is pyridyl (e.g. pyridin-3-yl), pyrazin-2-yl, thiophenyl (e.g. thiophen-2-yl), 5-phenyl-oxazol4-yl, 1-phenylsulfonyl-indol-2-yl, 3-methyl-5-phenyl-isoxazol4-yl, 3-phenyl-5-methyl-isoxazol4-yl, benzofuranyl (e.g. benzofuran-2-yl, benzofuran-5-yl or benzofuran-6-yl), benzothiophenyl (e.g. benzothiophen-2-yl), 4-phenyl4-thiophen-2-yl, 5-methyl-thiophen-2-yl, 3-chloro-6-methyl-benzothiophen-2-yl, 3-chloro-benzothiophen-2-yl, 3,6-dichloro-benzothiophen-2-yl, or 5-nitro-benzothiophen-2-yl;

in a more interesting embodiment thereof

Rb is 3-methyl-5-phenyl-isoxazol-4-yl, 3-phenyl-5-methyl-isoxazol-4-yl, or pyridyl, pyrazinyl, such as e.g. pyridin-3-yl or pyrazin-2-yl, or thiophenyl, such as e.g. thiophen-2-yl, or benzothiophenyl, or benzofuranyl, such as e.g. benzothiophen-2-yl, benzofuran-2-yl, benzofuran-5-yl or benzofuran-6-yl, or thiophenyl substituted by 1-4C-alkyl, such as e.g. 5-methyl-thiophen-2-yl;

in a particular embodiment thereof

Rb is 3-methyl-5-phenyl-isoxazol-4-yl, thiophen-2-yl, benzothiophen-2-yl, or, especially, benzofuran-6-yl, 5-methyl-thiophen-2-yl or pyridin-3-yl.

A notable subvariant (variant a14) of the compounds according to variant a of this invention includes those compounds of formula I, in which Rb is benzofuran-6-yl, 5-methyl-4-thiophen-2-yl or pyridin-3-yl.

A second variant (variant b) of the compounds according to this invention includes those compounds of formula I, in which Rb is Cyc.

A subvariant (variant b1) of the compounds according to variant b of this invention includes those compounds of formula I, in which Rb is Cyc, in which Cyc is 1,3-benzodioxolyl, 2,3-dihydro-1,4-benzodioxinyl, or 2,3-dihydrobenzofuranyl.

A more precise subvariant (variant b11) of the compounds according to variant b of this invention includes those compounds of formula I, in which Rb is Cyc, in which Cyc is 1,3-benzodioxol-5-yl, 2,3-dihydro-1,4-benzodioxin-5-yl, or 2,3-dihydrobenzofuran-6-yl.

A notable subvariant (variant b12) of the compounds according to variant b of this invention includes those compounds of formula I, in which Rb is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,3-dihydro-benzofuran-4-yl, 2,3-dihydro-benzofuran-5-yl, 2,3-dihydro-benzofuran-6-yl or 2,3-dihydro-benzofuran-7-yl.

A more notable subvariant (variant b13) of the compounds according to variant b of this invention includes those compounds of formula I, in which Rb is 2,3-dihydro-benzofuran-6-yl.

A third variant (variant c) of the compounds according to this invention includes those compounds of formula I, in which Rb is chromenyl.

A subvariant (variant c1) of the compounds according to variant c of this invention includes those compounds of formula I, in which Rb is Cyc, in which Cyc is chromen-3-yl.

A special concern of the present invention refers to those compounds according to this invention which are included by one or, when possible, by more of the following embodiments:

A special embodiment (embodiment 1) of the compounds according to this invention includes those compounds of formula I, in which Ra is —C(O)R1.

Particular compounds of embodiment 1 may include those compounds of formula I, in which Ra is —C(O)R1, in which R1 is 1-7C-alkyl, such as e.g. methyl, propyl, or hexyl.

Yet particular compounds of embodiment 1 may include those compounds of formula I, in which
Ra is —C(O)R1, in which
R1 is methyl, ethyl, propyl or butyl.

Another special embodiment (embodiment 2) of the compounds according to this invention includes those compounds of formula I, in which
Ra is —C(O)OR2.

Particular compounds of embodiment 2 may include those compounds of formula I, in which
Ra is —C(O)OR2, in which
R2 is 1-7C-alkyl, such as e.g. methyl, ethyl, tertbutyl, or pentyl, particularly ethyl.

Yet particular compounds of embodiment 2 may include those compounds of formula I, in which
Ra is —C(O)OR2, in which
R2 is methyl, ethyl, propyl or butyl.

More particular compounds of embodiment 2 may include those compounds of formula I, in which
Ra is —C(O)OR2, in which
R2 is ethyl.

Another special embodiment (embodiment 3) of the compounds according to this invention includes those compounds of formula I, in which
Ra is —C(O)SR2.

Particular compounds of embodiment 3 may include those compounds of formula I, in which
Ra is —C(O)SR2, in which
R1 is 1-7C-alkyl, such as e.g. ethyl.

Yet particular compounds of embodiment 3 may include those compounds of formula I, in which
Ra is —C(O)SR2, in which
R2 is methyl, ethyl, propyl or butyl.

More particular compounds of embodiment 3 may include those compounds of formula I, in which
Ra is —C(O)SR2, in which
R2 is ethyl.

Another special embodiment (embodiment 4) of the compounds according to this invention includes those compounds of formula I, in which
Ra is —C(O)N(R3)R4.

Another special embodiment (embodiment 5) of the compounds according to this invention includes those compounds of formula I, in which
Ra is —S(O)$_2$R1.

Another special embodiment (embodiment 6) of the compounds according to this invention includes those compounds of formula I, in which
Ra is —S(O)$_2$N(R3)R4.

Among these aforementioned embodiments, the embodiments 1 and 2 and 3 are to be emphasized.

Another special embodiment (embodiment 7) of the compounds according to this invention includes those compounds of formula I, in which
Rb is optionally substituted by Rca and/or Rcb, and is Har.

Particular compounds of embodiment 7 may include those compounds of formula I, in which
Rb is optionally substituted by Rca, and is Har, in which
Har is thiophenyl,
Rca is 1-4C-alkyl, such as e.g. methyl,
such as, for example, thiophen-2-yl, or, especially, 2-methyl-thiophen-5-yl.

Yet particular compounds of embodiment 7 may include those compounds of formula I, in which
Rb is Har, in which
Har is pyridyl,
such as, for example, pyridin-3-yl.

Still yet particular compounds of embodiment 7 may include those compounds of formula I, in which
Rb is Har, in which
Har is benzofuranyl,
such as, for example, benzofuran-5-yl or, especially, benzofuran-6-yl.

Another special embodiment (embodiment 8) of the compounds according to this invention includes those compounds of formula I, in which
Rb is Cyc.

Particular compounds of embodiment 8 may include those compounds of formula I, in which
Rb is Cyc, in which
Cyc is 2,3-dihydrobenzofuranyl,
such as, for example, 2,3-dihydrobenzofuran-5-yl, or, especially, 2,3-dihydrobenzofuran-6-yl.

Another special embodiment (embodiment 9) of the compounds according to this invention includes those compounds of formula I, in which
Rb is chromenyl, such as e.g. chromen-3-yl.

Another special embodiment (embodiment 10) of the compounds according to this invention includes those compounds of formula I, in which
Rb is any one of chromen-3-yl, benzofuran-5-yl, benzofuran-6-yl, 2,3-dihydrobenzofuran-5-yl, 2,3-dihydrobenzofuran-6-yl, 3-methyl-5-phenyl-isoxazol-4-yl, thiophen-2-yl, benzothiophen-2-yl, 5-methyl-thiophen-2-yl and pyridin-3-yl.

Particular compounds of embodiment 10 may include those compounds of formula I, in which
Rb is 5-methyl-thiophen-2-yl, benzofuran-5-yl, or pyridin-3-yl.

Yet particular compounds of embodiment 10 may include those compounds of formula I, in which
Rb is benzofuran-6-yl, 2,3-dihydrobenzofuran-6-yl, 5-methyl-thiophen-2-yl or pyridin-3-yl.

Another special embodiment (embodiment 11) of the compounds according to this invention includes those compounds of formula I, in which
Rb is CycA, in which
CycA is a group of formula U

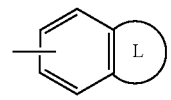

(U)

in which
L is a 5- or 6-membered unsaturated, aromatic heterocyclic ring comprising one to three heteroatoms independently selected from the group consisting of nitrogen, —N(Rdc)—, oxygen and sulfur, in which
Rdc is 1-4C-alkyl, or 1-4C-alkylcarbonyl,
whereby said CycA ring system is attached to the parent molecular group via a substitutable benzoring carbon atom,
such as for example benzofuran-5-yl or benzofuran-6-yl.

Another special embodiment (embodiment 12) of the compounds according to this invention includes those compounds of formula I, in which
Rb is Cyc or CycA.

Among these aforementioned embodiments, the embodiments 7, 8 and 10 are to be emphasized.

A group of compounds according to special embodiment I of the compounds according to this invention may include those compounds of formula I, in which Ra is —C(O)R1, in which RI is a radical selected from the following List 1.

List 1 consists of the following radicals:

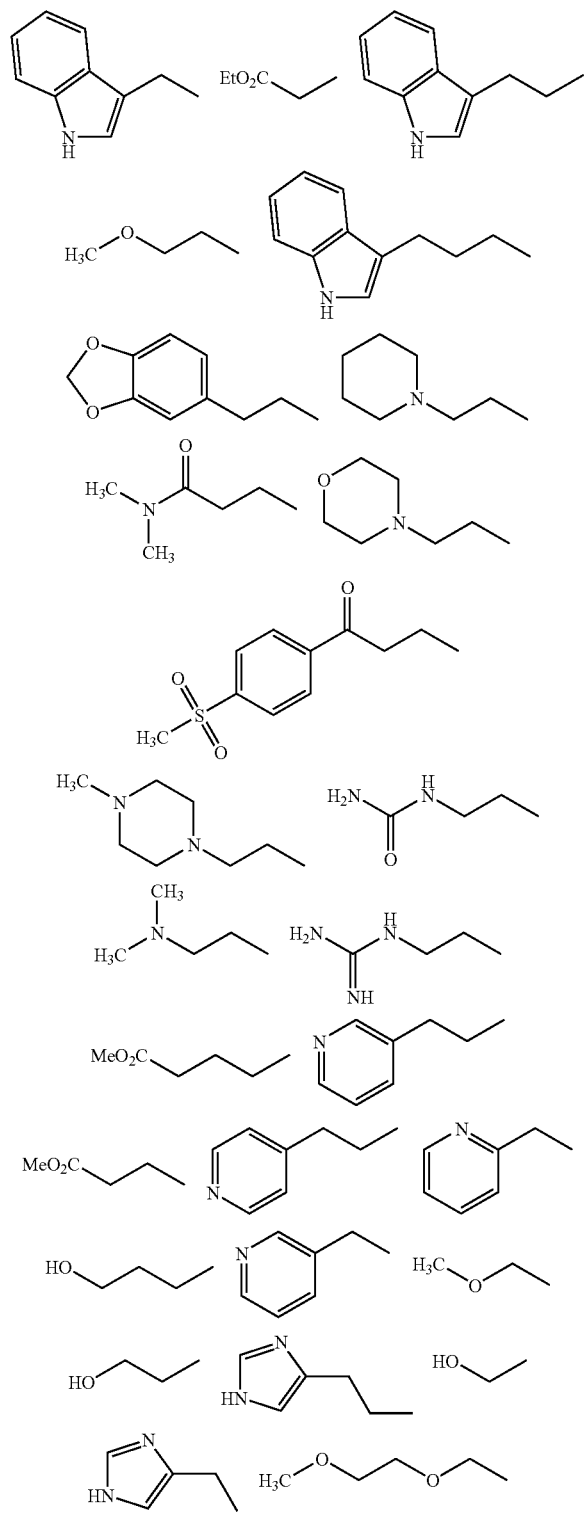
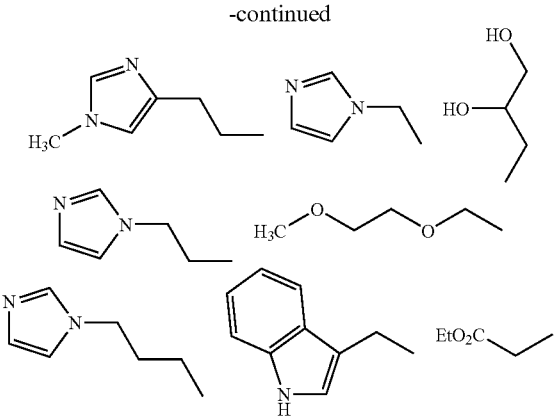

Another group of compounds according to this invention includes those compounds of formula I, in which Ra is —C(O)R1, in which R1 is a radical selected from the List 1, Rb is chromen-3-yl, benzofuran-5-yl, 3-methyl-5-phenyl-isoxazol-4-yl, thiophen-2-yl, benzothiophen-2-yl, 5-methyl-thiophen-2-yl or pyridin-3-yl.

Another group of compounds according to this invention includes those compounds of formula I, in which Ra is —C(O)R1, in which R1 is a radical selected from the List 1, and Rb is benzofuran-6-yl, 2,3-dihydrobenzofuran-6-yl, 5-methyl-thiophen-2-yl or pyridin-3-yl.

A group of compounds according to special embodiment 2 of the compounds according to this invention may include those compounds of formula I, in which Ra is —C(O)OR2, in which R2 is a radical selected from the following List 2.

List 2 consists of the following radicals:

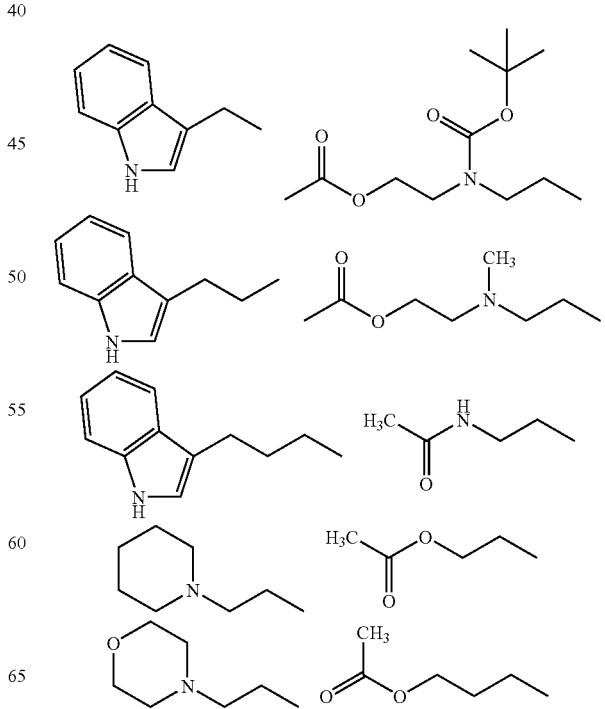

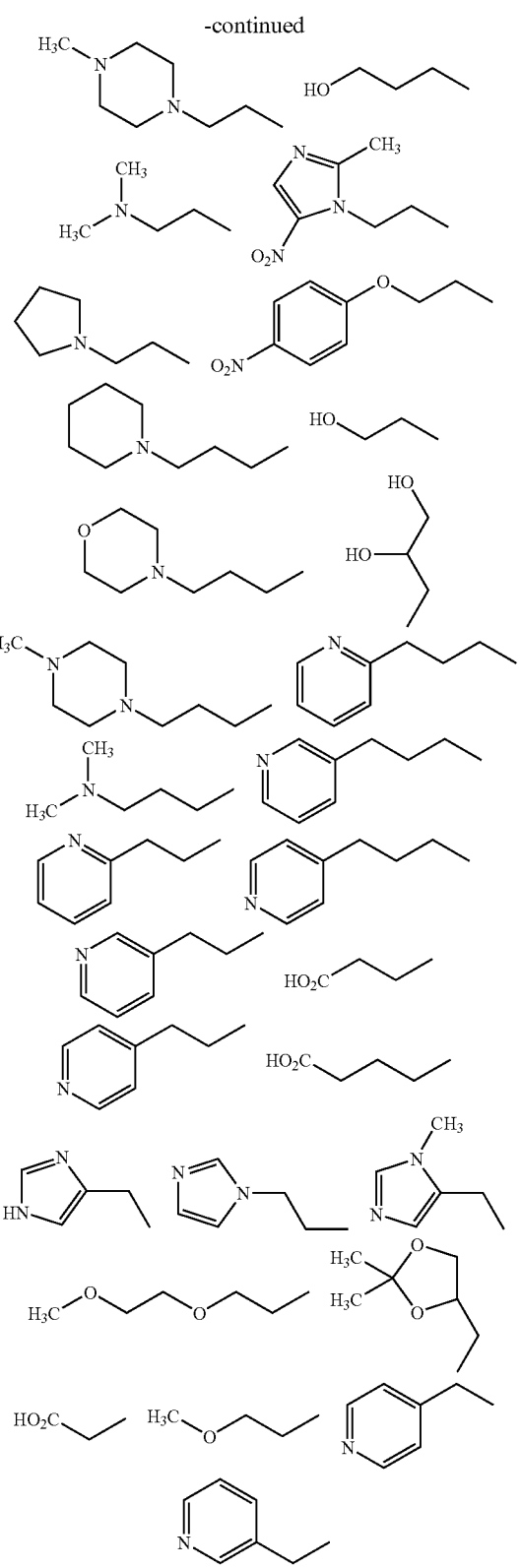

Another group of compounds according to this invention includes those compounds of formula I, in which
Ra is —C(O)OR2, in which
R2 is a radical selected from the List 2, Rb is chromen-3-yl, benzofuran-5-yl, 3-methyl-5-phenyl-isoxazol-4-yl, thiophen-2-yl, benzothiophen-2-yl, 5-methyl-thiophen-2-yl or pyridin-3-yl.

Another group of compounds according to this invention includes those compounds of formula I, in which
Ra is —C(O)OR2, in which
R2 is a radical selected from the List 2, and
Rb is benzofuran-6-yl, 2,3-dihydrobenzofuran-6-yl, 5-methyl-thiophen-2-yl or pyridin-3-yl.

A group of compounds according to special embodiment 3 of the compounds according to this invention may include those compounds of formula I, in which
Ra is —C(O)SR2,
in which R2 is a radical selected from the following List 3.
List 3 consists of the following radicals:

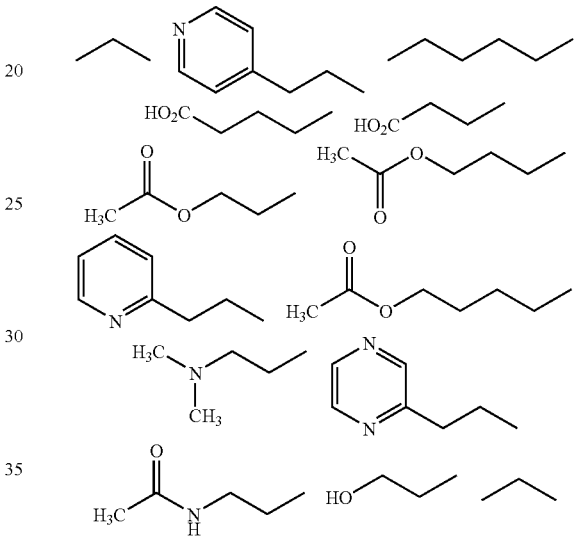

Another group of compounds according to this invention includes those compounds of formula I, in which
Ra is —C(O)SR2, in which
R2 is a radical selected from the List 3,
Rb is chromen-3-yl, benzofuran-5-yl, 3-methyl-5-phenyl-isoxazol-4-yl, thiophen-2-yl, benzothiophen-2-yl, 5-methyl-thiophen-2-yl or pyridin-3-yl.

Another group of compounds according to this invention includes those compounds of formula I, in which
Ra is —C(O)SR2, in which
R2 is a radical selected from the List 3, and
Rb is benzofuran-6-yl, 2,3-dihydrobenzofuran-6-yl, 5-methyl-thiophen-2-yl or pyridin-3-yl.

Compounds according to the present invention can be prepared as described below or as shown in the following reaction schemes, or as disclosed in WO2004l024066 or, particularly, WO2004/024065, the disclosure of which is incorporated herein, or similarly or analogously thereto according to preparation procedures or synthesis strategies known to the person skilled in the art. Accordingly, compounds according to the present invention can be obtained as specified by way of example in the following examples, or similarly or analogously thereto.

Thus, as shown in reaction scheme below, a compound of formula III, in which Ra has the meanings given above, can be condensed with malonitrile in the presence of sulfur and a suitable base, such as for example an amine (e.g. diethyl amine or morpholine) to give corresponding compounds of formula II in a manner known to the person skilled in the art (e.g. according to a Gewald reaction) or as described in the following examples.

Compounds of formula III are known or can be obtained in an art-known manner.

Compounds of formula II can be reacted with compounds of formula Rb—C(O)—X, in which Rb has the meanings mentioned above and X is a suitable leaving group, preferably a chlorine atom, in an acylation reaction under conditions habitual per se to give the desired compounds of formula I, in which Ra and Rb have the meanings given above.

Alternatively, compounds of the formula I can also be prepared from the corresponding compounds of formula II and corresponding compounds of formula Rb—C(O)—X, in which X is hydroxyl, by reaction with amide bond linking reagents known to the person skilled in the art. Exemplary amide bond linking reagents known to the person skilled in the art which may be mentioned are, for example, the carbodiimides (e.g. dicyclohexylcarbodiimide or, preferably, 1-ethyl-3-(3-dimethylaminopropyl)carbodiimide hydrochloride), azodicarboxylic acid derivatives (e.g. diethyl azodicarboxylate), uronium salts [e.g. O-(benzotriazol-1-yl)-N,N,N',N'-tetramethyluronium tetrafluoroborate or O-(benzotriazol-1-yl)-N,N, N',N'-tetramthyl-uronium-hexafluorophosphate] and N,N'-carbonyidiimidazole. In the scope of this invention preferred amide bond linking reagents are uronium salts and, particularly, carbodiimides, preferably, 1-ethyl-3-(3-dimethylaminopropyl)carbodiimide hydrochloride (EDC).

in "Protecting Groups (Thieme Foundations Organic Chemistry Series N Group" by P. Kocienski (Thieme Medical Publishers, 2000), can be condensed with malonitrile in the presence of sulfur and a suitable base as described above to give corresponding compounds of formula V. Compounds of formula VI are known or can be obtained in an art-known manner. Compounds of formula V can be acylated with compounds of formula Rb—C(O)—X analogously as mentioned above. Subsequential deprotection of the protective group PG in a manner customary per se for the skilled person gives compounds of formula IV, in which Rb has the meanings as mentioned above.

Compounds of formula IV can be converted into desired compounds of formula I by introduction of the group Ra via methods known to one of ordinary skill in the art.

More specifically, for example, compounds of the formula I, in which a) Ra is an acyl group, can be prepared from compounds of formula IV by acylation reaction;
b) Ra is a sulfonyl group, can be obtained from compounds of formula IV by sulfonylation reaction;
c) Ra is an ester group, can be obtained from compounds of formula IV by carbamate formation reaction;
d) Ra is an amide group, can be prepared from compounds of formula IV by urea formation reaction;
e) Ra is a thioester group, can be prepared from compounds of formula IV by thiocarbamate formation reaction;

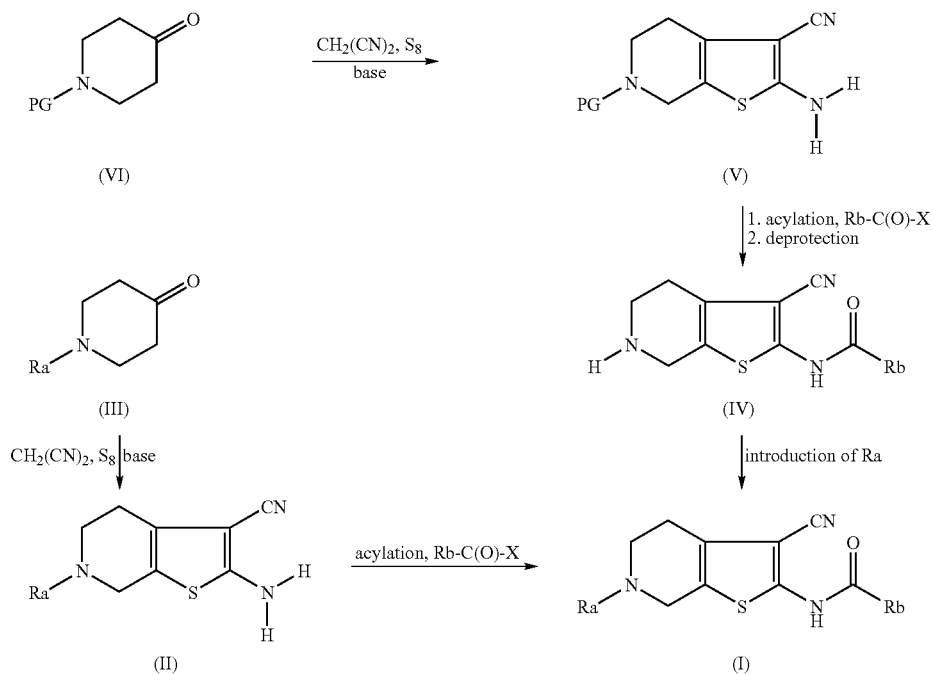

Acid derivatives of formula Rb—C(O)—X are known, commercially available or can be prepared as it is known for the skilled person, e.g. from the corresponding carboxylic acids.

In an alternative synthesis route, compounds of formula VI, in which PG is a suitable temporary protective group, such as for example tertbutoxycarbonyl (Boc) or one of those mentioned in "Protective Groups in Organic Synthesis" by T. Greene and P. Wuts (John Wiley & Sons, Inc. 1999, 3$^{rd}$ Ed.) or f.) Ra is a sulfonamide group, can be prepared from compounds of formula IV by sulfamide formation reaction.

The methods mentioned under a) to f) are expediently carried out analogously to the methods known to the person skilled in the art or as described by way of example in the following examples. The appropriate starting compounds used in the methods mentioned under a) to f) are art-known or can be obtained according to art-known procedures.

Thus, for example, when 3-(Har)-propionic acids in which Har has the meanings given above (e.g. pyridyl) are used as starting compounds in the method mentioned under a.), these compounds can be obtained via CC-coupling reactions, such as e.g. by Heck reaction or, starting from aldehydes of the formula Har-CHO, by Knoevenagel or Homer-Wadsworth-Emmons reaction, and hydration reaction.

It is to be understood for the skilled worker, that certain compounds of formula I according to this invention can be converted into further compounds of formula I by art-known synthesis strategies and reactions habitual per se to a person of ordinary skill in the art.

Therefore, optionally, compounds of formula I can be converted into further compounds of formula I by methods known to one of ordinary skill in the art. More specifically, for example, from compounds of the formula I in which i) R5 is acyloxy, such as e.g. acetoxy, the corresponding free hydroxyl compounds can be obtained by removal of the acyl group, such as e.g. by saponification reaction;
ii) Het is a cyclic acetal or ketal, such as e.g. the 2,2-dimethyl-[1,3]dioxolan acetal, the corresponding free dihydroxy compounds can be obtained by cleavage of the acetal or ketal, such as e.g. by deacetalization reaction;
iii) R5 is an ester group, such as e.g. methoxycarbonyl, the corresponding free carboxyl compounds can be obtained by deesterification reaction, such as e.g. by saponification reaction.

The methods mentioned under i) to iii) can be expediently carried out analogously to the methods known to the person skilled in the art.

Optionally, compounds of the formula I can be converted into their salts, or, optionally, salts of the compounds of the formula I can be converted into the free compounds. Corresponding processes are habitual per se to the skilled person.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of formula I. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations, alternatives and adaptations to the described invention can be made on the base of art-known knowledge and/or, particularly, on the base of the disclosure (e.g. the explicite, implicite or inherent disclosure) of the present invention without departing from the spirit and scope of this invention as defined by the appended claims.

The following examples serve to illustrate the invention further without restricting it. Likewise, further compounds of formula I, whose preparation is not explicitly described, can be prepared in an analogous or similar manner or in a manner familiar per se to the person skilled in the art using customary process techniques.

Any or all of the compounds of formula I according to the present invention which are mentioned in the following examples, particularly which are mentioned as final compounds, as well as their salts are a preferred subject of the present invention.

In the examples, MS stands for mass spectrum, calc. for calculated, fnd. for found, Boc for the tertbutoxycarbonyl group, EDC for 1-ethyl-3-(3-dimethylaminopropyl)carbodiimide hydrochloride and other abbreviations have their meanings customary per se to the skilled person.

EXAMPLES

Final Compounds:

1. N-(6-ethoxycarbonyl-3-cyano-4,5,6,7-tetrahydro-thieno[2,3-c]pyridin-2-yl)-nicotinyl Amide

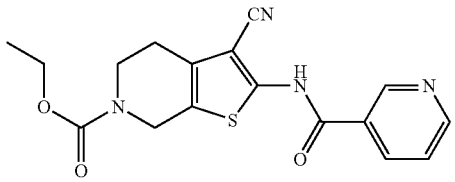

Prepared according to general procedure A described below starting from 2-amino-3-cyano-4,7-dihydro-thieno[2,3-c]pyridine-6(5H)-carboxylic acid ethyl ester (compound A1) and nicotinoyl acid chloride.

MS: calc.: $C_{17}H_{16}N_4O_3S$ (356.41) fnd.: 357.0 [M+H]

2. N-(6-tert.-butyloxycarbonyl-3-cyano-4,5,6,7-tetrahydro-thieno[2,3-c]pyridin-2-yl)-nicotinyl Amide

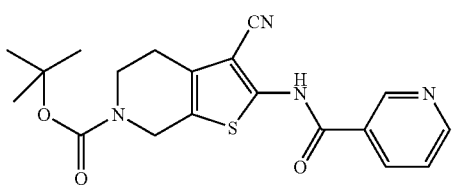

Prepared according to general procedure A described below starting from 2-amino-3-cyano-4,7-dihydro-thieno[2,3-c]pyridine-6(5H)-carboxylic acid 1,1-dimethylethyl ester (compound A2) and nicotinoyl acid chloride.

MS: calc.: $C_{19}H_{20}N_4O_3S$ (384.46) fnd.: 384.9 [M+H]

The following compounds can be prepared according to general procedure A described below starting from 2-amino-3-cyano-4,7-dihydro-thieno[2,3-c]pyridine-6(5H)-carboxylic acid ethyl ester (compound A1) and the appropriate carboxylic acid derivatives.

3. 3-Cyano-2-{[1-(5-phenyl-oxazol4-yl)-methanoyl]-amino}-4,7-dihydro-5H-thieno[2,3-c]pyridine-6-carboxylic Acid Ethyl Ester

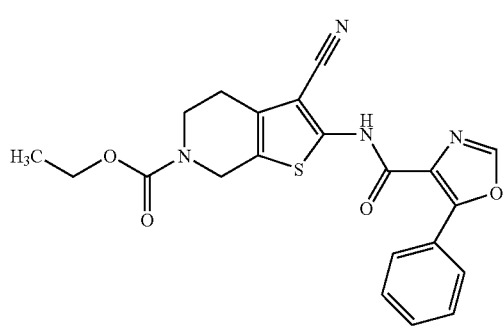

MS: calc.: $C_{21},H_{18}N_4O_4S$ (422,47) fnd.: 423 [M+H]

4. 2-{[1-(1-Benzenesulfonyl-1H-indol-2-yl)-methanoyl]-amino}-3-cyano-4,7-dihydro-5H-thieno [2,3-c]pyridine-6-carboxylic Acid Ethyl Ester

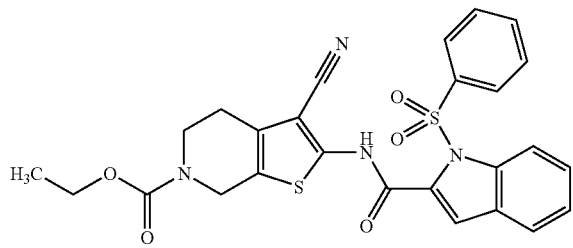

MS: calc.: $C_{26}H_{22}N_4O_5S_2$ (534,62) fnd.: 534,9 [M+H]

5. 3-Cyano-2-{[1-(3-methyl-5-phenyl-isoxazol-4-yl)-methanoyl]-amino}-4,7-dihydro-5H-thieno [2,3-c]pyridine-6-carboxylic Acid Ethyl Ester

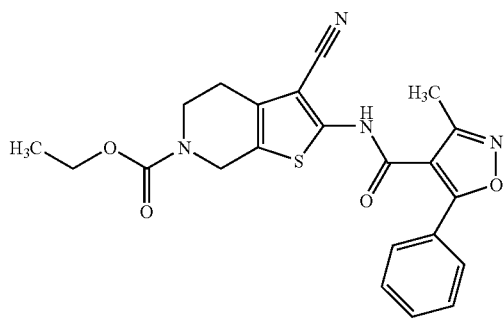

MS: calc.: $C_{22}H_{20}N_4O_4S$ (436,49) fnd.: 437 [M+H]

6. 2-[(1-2H-Chromen-3-yl-methanoyl)-amino]-3-cyano-4,7-dihydro-5H-thieno[2,3-c]pyridine-6-carboxylic Acid Ethyl Ester

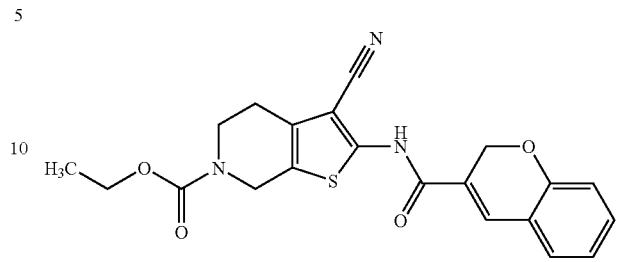

MS: calc.: $C_{21}H_{19}N_3O_4S$ (409,47) fnd.: 410 [M+H]

7. 3-Cyano-2-[(1-thiophen-2-yl-methanoyl)-amino]-4,7-dihydro-5H-thieno[2,3-c]pyridine-6-carboxylic Acid Ethyl Ester

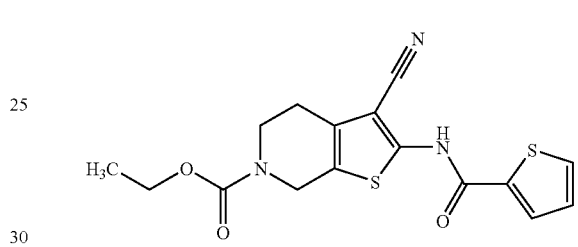

MS: calc.: $C_{16}H_{15}N_3O_3S_2$ (361,44) fnd.: 362,1 [M+H]

8. 2-[(1-Benzo[b]thiophen-2-yl-methanoyl)-amino]-3-cyano-4,7-dihydro-5H-thieno[2,3-c]pyridine-6-carboxylic Acid Ethyl Ester

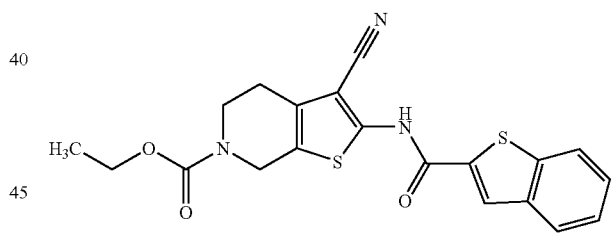

MS: calc.: $C_{20}H_{17}N_3O_3S_2$ (411,5) fnd.: 412,1 [M+H]

9. 3-Cyano-2-{[1-(4-phenyl-thiophen-2-yl)-methanoyl]-amino}-4,7-dihydro-5H-thieno[2,3-c]pyridine-6-carboxylic Acid Ethyl Ester

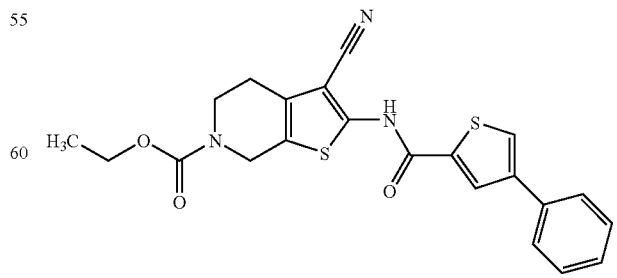

MS: calc.: $C_{22}H_{19}N_3O_3S_2$ (437,54) fnd.: 438 [M+H]

10. 3-Cyano-2-{[1-(5-methyl-thiophen-2-yl)-methanoyl]-amino}-4,7-dihydro-5H-thieno[2,3-c]pyridine-6-carboxylic Acid Ethyl Ester

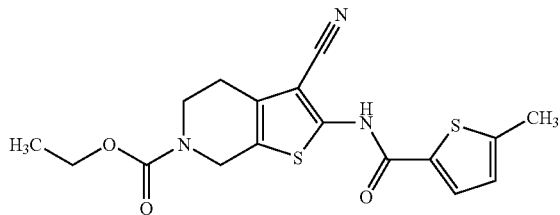

MS: calc.: $C_{17}H_{17}N_3O_3S_2$ (375,47) fnd.: 376 [M+H]

11. 2-[(1-Benzo[b]furan-5-yl-methanoyl)-amino]-3-cyano-4,7-dihydro-5H-thieno[2,3-c]pyridine-6-carboxylic Acid Ethyl Ester

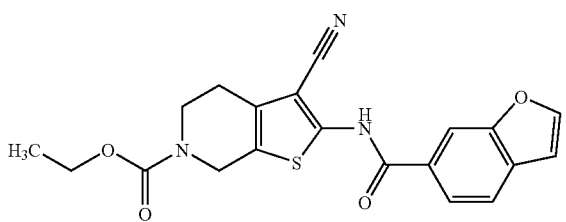

MS: calc.: $C_{20}H_{17}N_3O_4S_2$ (395,44) fnd.: 396,1 [M+H]

12. 2-[(1-2,3-Dihydro-benzo[b]furan)-6-yl-methanoyl)-amino]-3-cyano-4,7-dihydro-5H-thieno [2,3-c]pyridine-6-carboxylic Acid Ethyl Ester

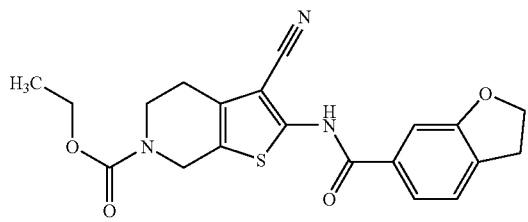

13. N-(6-Acetyl-3-cyano-4,5,6,7-tetrahydro-thieno[2,3-c]pyridin-2-yl)-nicotinyl Amide

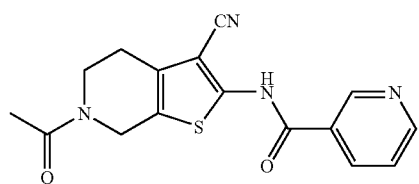

Prepared according to general procedure A starting from 6-acetyl-2-amino-3-cyano-4,5,6,7-tetrahydro-thieno [2,3-c]pyridine (compound A3) and nicotinyl acid chloride.

MS: calc.: $C_{16}H_{14}N_4O_2S$ (326.38) fnd.: 327.1 [M+H]

14. N-(6-Butanoyl-3-cyano-4,5,6,7-tetrahydro-thieno[2,3-c]pyridin-2-yl)-nicotinyl Amide

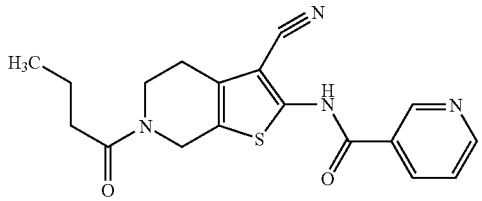

Prepared according to general procedure A starting from N-(3-cyano-4,5,6,7-tetrahydro-thieno[2,3-c]pyridin-2-yl)-nicotinyl amide (compound B1) and butanoyl chloride.

15. 2-[(1-(2,3-Dihydro-benzo[b]furan)-6-yl-methanoyl)-amino]-3-cyano-4,7-dihydro-5H-thieno [2,3-c]pyridine-6-carboxylic Acid Tertbutyl Ester

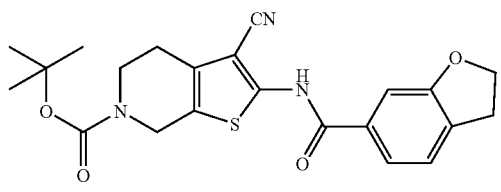

Prepared according to general procedure A described below starting from 2-amino-3-cyano-4,7-dihydro-thieno [2,3-c]pyridine-6(5H)-carboxylic acid 1, 1-dimethylethyl ester (compound A2) and 2,3-dihydrofuran-6-carboxylic acid.

MS: calc.: C22 H23 N3 O4 S (325,51)

16. 3-Cyano-2-[(1-pyridin-3-yl-methanoyl)-amino]-4,7-dihydro-5H-thieno[2,3-c]pyridine-6-carbothioic Acid S-ethyl Ester

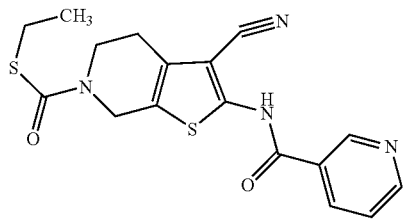

To a suspension of N-(3-cyano-4,5,6,7-tetrahydro-thieno [2,3-c]pyridin-2-yl)-nicotinamide (1 mmol) and ethylthio-chloroformiate (1 mmole) in abs. dichloromethane (20 ml), DBU (1.2 mmol) is added, the mixture is stirred for 1 to 2 days, the reaction is monitored by TLC (silica, dichloromethane-ethyl acetate 10:1 mixture as an eluent). The reaction mixture is extracted twice by 10% sodium hydrogencarbonate solution, once by water, and the organic layer is dried over sodium sulfate. After evaporation the residue is purified by column chromatography.

MS: calc.: C17 H16 N4 O2 S2 (372,47) fnd.: 372 [M+H]

17. 3-Cyano-2-[(1-Pyridin -3-yl-methanoyl)-amino]-4,7-dihydro-5H-thieno[2,3-c]pyridine-6-carboxylic Acid 2-(4-methyl-thiazol-5-yl)-ethyl Ester

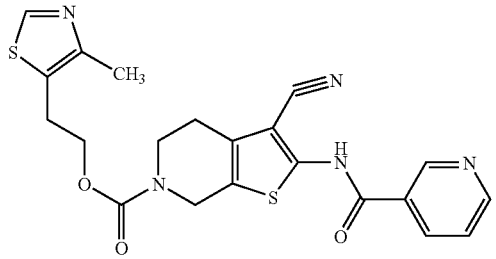

The title compound can e prepared according to general procedure E given below starting from N-(3-cyano-4,5,6,7-tetrahydro-thieno[2,3-c]pyridin-2-yl)-nicotinamide and the appropriate alcohol.

MS: calc.: C21 H19 N5 O3 S2 (453,55) fnd.: 454,2 [M+H]

A. General Procedure for Amide Bond Formation a) 100 mmol of an amine and 120 mmol of an appropriate acid chloride (which can be obtained in an art-known manner from the corresponding free acid, such as e.g. with the aid of oxalyl chloride) are dissolved either in a minimal amount of pyridine or toluene. In case of toluene as solvent, 125 mmol of a base (e.g. triethylamine) is added. The reaction mixture is stirred for some time at room temperature and, if necessary, is heated for some time either by conventional or microwave assisted heating. Then the solvent is either removed in vacuo or the reaction mixture partitioned between water and an appropriate solvent (e.g. ethyl acetate). In the second case, the aqueous layer is extracted several times with the organic solvent, the combined organic layers are dried (e.g. MgSO$_4$) and concentrated in vacuo. Purification of the crude product is achieved by flash chromatography and/or recristalization from an appropriate solvent (e.g. ethanol).

In some cases, the amide bond formation reaction is carried out using one of the following methods:

b) 20 mmol of a carboxylic acid and 20 mmol of EDC are dissolved or suspended in an appropriate solvent (e.g. dichloromethane) and 10 mmol of the amine and 0.1 mmol N,N-dimethylaminopyridine (DMAP) are added. After stirring for several hours at room temperature (If necessary, the reaction mixture is heated either by conventional heating or microwave assisted heating.), the reaction mixture is partitioned between water and an appropriate solvent (e.g. ethyl acetate or dichloromethane) and the aqueous layer is extracted several times with the same organic solvent. The combined organic layers are dried (e.g. MgSO$_4$) and concentrated in vacuo. Purification of the crude product is achieved by flash chromatography and/or recristalization from an appropriate solvent (e.g. ethanol).

Starting Materials:

A1. 2-Amino-3-cyano-4,7-dihydro-thieno[2,3-c]pyridine-6(5H)-carboxylic Acid Ethyl Ester

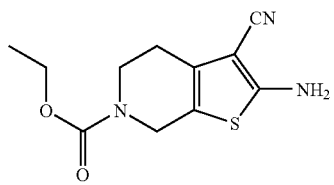

Prepared according to general procedure B decribed below starting from N-carbethoxy-4-piperidone.

MS: calc.: $C_{11}H_{13}N_3O_2S$ (251.31) fnd.: 252.0 [M+H]

B. General Procedure for Condensed 2-amino-thiophene-3-carbonitrile Derivatives 500 mmol of cyclic ketone and 500 mmol of malononitrile are dissolved in a minimal volume of ethanol and 500 mmol elemental sulfur are added. After addition of 500 mmol diethyl amine, the reaction mixture is heated to 60-70° C. for some minutes and then stirred at room temperature for several hours. The reaction mixture is poured on ice/water and the precipitate filtered off. In case there is no or only some precipitate formed, the aqueous layer is extracted several times with dichloromethane or another appropriate organic solvent, the combined organic layers are dried (e.g. MgSO$_4$) and concentrated in vacuo. Purification of the crude product is achieved by flash chromatography and/or recristallization from an appropriate solvent (e.g. ethanol).

A2. 2-Amino-3-cyano-4,7-dihydro-thieno[2,3-c]pyridine-6(5H)-carboxylic Acid 1,1-dimethylethyl Ester

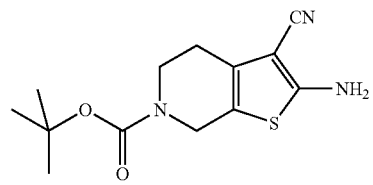

Prepared according to general procedure B starting from Boc-piperidone.

MS: calc.: $C_{13}H_{17}NO_2S$ (279.36) fnd.: 280.0 [M+H]

A3. 6-Acetyl-2-amino-3-cyano-4,5,6,7-tetrahydro-thieno[2,3-c]pyridine

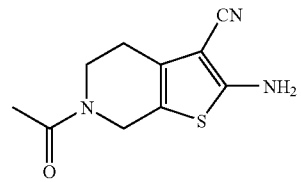

Prepared according to general procedure B starting from acetyl-4-piperidone.

MS: calc.: $C_{10}H_{11}N_3OS$ (221.28) fnd.: 222.0 [M+H]

B1. N-(3-Cyano-4,5,6,7-tetrahydro-thieno[2,3-c]pyridin-2-yl)-nicotinyl amide

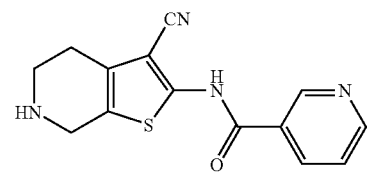

Prepared according to general procedure C starting from N-(6-tert.-butyloxycarbonyl-3-cyano4,5,6,7-tetrahydro-thieno [2,3-c]pyridin-2-yl)-nicotinyl amide (compound 2).

MS: calc.: $C_{14}H_{12}N_4OS$ (284.34) fnd.: 285.0 [M+H]

B2. N-(3-Cyano-4,5,6,7-tetrahydro-thieno[2,3-c]pyridin-2-yl)-(2,3-dihydro-benzo[b]furan)-6-carboxylic Acid Amide

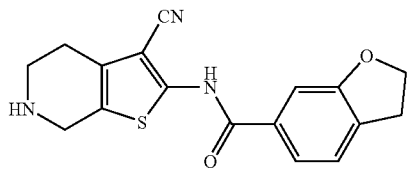

The title compound can be prepared according to compound BI starting from compound 15.

C. General Procedure for Removal of Boc Protecting Groups

The Boc protected compound is dissolved in dichloromethane/trifluoroacetic acid (TFA) (2/3) and stirred for several hours at room temperature. After evaporation of the solvent and recristalization from an appropriate solvent (e.g. ethanol), the desired product is obtained as TFA salt. The TFA salt may be converted into the free base in a manner customary per se to the skilled person.

D. General Procedure for Sulfonamide Bond Formation 100 mmol of the amine and 150 mmol of the sulfonyl chloride are dissolved in pyridine and stirred for some time at room temperature and, if necessary, is heated for some time either by conventional or microwave assisted heating. Then the solvent is either removed in vacuo or the reaction mixture is partitioned between water and an appropriate solvent (e.g. ethyl acetate). In the second case, the aqueous layer is extracted several times with the organic solvent, the combined organic layers are dried (e.g. MgSO$_4$) and concentrated in vacuo. Purification of the crude product is achieved by flash chromatography and/or recristalization from an appropriate solvent (e.g. ethanol).

E. General Procedure for Carbamate Formation 100 mmol pyridine and 65 mmol triphosgene are dissolved in dichloromethane. 65 mmol of the alcohol are added at 0C and the reaction is stirred at room temperature for 3 hours. This solution is added to 200 mmol of the amine in dichloromethane at −78° C. and the reaction mixture is allowed to warm to room temperature and stirred for some time. Then the solvent is either removed in vacuo or the reaction mixture is partitioned between water and an appropriate solvent (e.g. ethyl acetate). In the second case, the aqueous layer is extracted several times with the organic solvent, the combined organic layers are dried (e.g. MgSO$_4$) and concentrated in vacuo. Purification of the crude product is achieved by flash chromatography and/or recristalization from an appropriate solvent (e.g. ethanol).

It is to be stated, that, starting from the starting compounds, which are mentioned herein or which can be prepared analogously to the herein-mentioned compounds, the person skilled in the art can apply—on the base of his/her expert knowledge, general art and/or analogous or similar art-known procedures —the general procedures described herein to the synthesis of those specific examples given herein and further specific examples encompassed from the scope of the present invention.

COMMERCIAL APPLICABILITY

The compounds according to the present invention have miscellaneous valuable pharmacological properties which can make them commercially applicable. The compounds according to the invention therefore can be employed as therapeutic agents for the treatment and/or prophylaxis of diseases in human and veterinary medicine.

Thus, for example, in more embodimental detail, the compounds according to this invention are potent and highly efficacious cell-cycle specific inhibitors of cellular (hyper) proliferation and/or inducers of apoptosis in cancer cells. Therefore, these compounds are expected to be useful for treating (hyper)proliferative diseases and/or disorders responsive to the induction of apoptosis, in particular cancer.

Further on, these compounds can be useful in the treatment of benign or malignant neoplasia. A "neoplasia" is defined by cells displaying aberrant cell proliferation and/or survival and/or a block in differentiation. A "benign neoplasia" is described by hyperproliferation of cells, incapable of forming an aggressive, metastasizing tumor in-vivo. In contrast, a "malignant neoplasia" is described by cells with multiple cellular and biochemical abnormalities, capable of forming a systemic disease, for example forming tumor metastasis in distant organs.

Various diseases are caused by limitless replicative potential and aberrant cell proliferation ("hyperproliferation") as well as evasion from apoptosis. These diseases include benign hypoplasia like that of the prostate ("BPH") or colon epithelium, psoriasias, glomerulonephritis or osteoarthritis. Most importantly these diseases include malignant neoplasia commonly described as cancer and characterized by tumor cells finally metastasizing into distinct organs or tissues. Malignant neoplasia include solid and hematological tumors. Solid tumors are exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva. Malignant neoplasias include inherited cancers exemplified by Retinomblastoma and Wilms tumor. In addition, malignant neoplasia include primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Compounds according to the present invention will commercially applicable for treatment, prevention or amelioration of the diseases of benign and malignant behavior as described before.

Neoplastic cell proliferation might effect normal cell behaviour and organ function. For example the formation of new blood vessels, a process described as neovascularization, is induced by tumors or tumor metastases. Compounds according to this invention will commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps or mutation within the cellular target protein. The commercial applicability of the compounds according to this invention is not limited to $1^{st}$ line treatment of patients. Patients with resistance to defined cancer chemotherapeutics or target specific anti-cancer drugs ($2^{nd}$ or $3^{rd}$ line treatment) are also amenable for treatment with the compounds according to this invention.

The compounds according to the present invention display a cell cycle dependent cytotoxic activity, more precisely a mitosis confined activity, leading to a mitotic arrest which inevitably results in the onset of apoptosis and/or cell death.

In the context of their properties, functions and usabilities mentioned herein, the compounds according to the present invention are expected to be distinguished by valuable and desirable effects related therewith, such as e.g. by low toxicity, superior bioavailability in general (such as e.g. good enteral absorption), superior therapeutic window, absence of significant side effects, and/or further beneficial effects related with their therapeutic and pharmaceutical suitability.

The invention further includes a method for treating (hyper)proliferative diseases and/or disorders responsive to the induction of apoptosis, particularly those diseases, disorders, conditions or illnesses mentioned above, in mammals, including humans, suffering therefrom comprising administering to said mammals in need thereof a pharmacologically active and therapeutically effective and tolerable amount of one or more of the compounds according to this invention.

The present invention further includes a therapeutic method useful to modulate apoptosis in vivo or aberrant cell growth in benign or malignant neoplastic diseases, such as e.g. cancer, comprising administering to a subject in need of such therapy a therapeutically active and pharmacologically effective and tolerable amount of one or more of the compounds according to this invention which function by arresting aberrant cell growth and/or inducing apoptosis.

The present invention further relates to the use of the compounds according to this invention for the production of pharmaceutical compositions which are employed for the treatment, prophylaxis and/or amelioration of the illnesses mentioned.

The present invention further relates to the use of the compounds according to this invention for the production of pharmaceutical compositions which can be used in the treatment, prevention or amelioration of (hyper)proliferative diseases of benign or malignant behaviour and/or disorders responsive to the induction of apoptosis in a mammal, such as, for example, benign or malignant neoplasia, particularly cancer.

The present invention further relates to the use of the compounds according to this invention for the production of pharmaceutical compositions which can be used use in the treatment, prevention or amelioration of disorders responsive to arresting of aberrant cell growth and/or induction of apoptosis.

The present invention further relates to pharmaceutical compositions comprising one or more of the compounds according to this invention and a pharmaceutically acceptable carrier or diluent.

The present invention further relates to pharmaceutical compositions made by combining one or more of the compounds according to this invention and a pharmaceutically acceptable carrier or diluent.

The present invention further relates to combinations comprising one or more of the compounds according to this invention and pharmaceutically acceptable auxiliaries, excipients or vehicles, e.g. for use in the treatment, prevention or amelioration of hyperproliferative diseases of benign or malignant behaviour and/or disorders responsive to the induction of apoptosis in a mammal, such as e.g. cancer.

The present invention further relates to a composition consisting essentially of a therapeutically effective and tolerable amount of one or more tetrahydropyridothiophen compounds according to this invention together with the usual pharmaceutically acceptable vehicles, diluents and/or excipients for use in therapy, e.g. for treating, preventing or ameliorating hyperproliferative diseases, such as e.g. cancer, and/or disorders responsive to induction of apoptosis.

The present invention further relates to compounds according to this invention for use in therapy, such as, for example, in the treatment, prevention or amelioration of (hyper)proliferative diseases of benign or malignant behaviour and/or disorders responsive to the induction of apoptosis, such as e.g. those diseases mentioned herein, particularly cancer.

The present invention further relates to compounds according to this invention having anti-proliferative and/or apoptosis inducing activity.

The present invention further relates to pharmaceutical compositions according to this invention having anti-proliferative activity.

The present invention further relates to pharmaceutical compositions according to this invention having apoptosis inducing activity.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Additionally, the invention relates to an article of manufacture, which comprises packaging material and a pharmaceutical agent contained within said packaging material, wherein the pharmaceutical agent is therapeutically effective inhibiting cellular (hyper)proliferation and/or inducing apoptosis, ameliorating the symptoms of a (hyper)proliferative disorder and/or a disease responsive to the induction of apoptosis, and wherein the packaging material comprises a label or package insert which indicates that the pharmaceutical agent is useful for preventing or treating a (hyper)proliferative disorder and/or a diseases responsive to the induction of apoptosis, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions according to this invention are prepared by processes which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

For example, the compounds according to this invention may be combined with one or more known anti-cancer chemotherapeutic agents and/or with other target specific anti-cancer agents as described below.

Examples of known chemotherapeutic anti-cancer agents frequently used for combination therapy include, but are not limited to (i) alkylating/carbamylating agents such as Cyclophosphamid (Endoxan®), Ifosfamid (Holoxan®), Thiotepa (Thiotehpa Ledede®), Melphalan (Alkeran®), or chloroethyinitrosourea (BCNU); (ii) platinum derivatives like cisplatin (Platinex® BMS), oxaliplatin or carboplatin (Cabroplat® BMS); (iii) antimitotic agents/tubulin inhibitors such as vinca alkaloids (vincristine, vinblastine, vinorelbine), taxanes such as Taxol (Paclitaxel®), Taxotere (Docetaxel®) and analogs as well as new formulations and conjugates thereof; (iv) topoisomerase inhibitors such as anthracyclines such as Doxorubicin (Adriblastin®), epipodophyllotoxines (such as Etoposide (Etopophos®) and camptothecin analogs such as Topotecan (Hycamtin®); (v) pyrimidine antagonists such as 5-fluorouracil (5-FU), Capeditabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) and pemetrexed (Alimta®).

Examples of target specific anti-cancer drug classes used in experimental or standard cancer therapy include but are not limited to (i) kinase inhibitors such as e.g. Glivec (Imatinib®), ZD-1839/Iressa (Gefitinib®), Bay43-9006 (Sorafenib®), SU11248 (Sutent®) or OSI-774/Tarceva (Erlotinib®); (ii) proteasome inhibitors such as PS-341 (Velcade®); (iii) histone deacetylase inhibitors like SAHA, PXD101, MS275, MGCD0103, Depsipeptide/FK228, NVP-LBH589, Valproic acid (VPA) and butyrates; (iv) heat shock protein inhibitors like 17-allylaminogeldanamycin (17-MG); (v) vascular targeting agents (VAT) and anti-angiogenic drugs like the VEGF antibody Avastin (Bevacizumab®) or the KDR tyrosine kinase inhibitor PTK787/ZK222584 (Vatalanib®); (vi) monoclonal antibodies such as Herceptin (Trastuzumab®) or MabThera/Rituxan (Rituximab®) or C225/Erbitux (Cetuximab®) as well as mutants and conjugates of monoclonal antibodies and antibody fragments; (vii) oligonucleotide based therapeutics like G-3139/Genasense (Oblimersen®); (viii) protease inhibitors (ix) hormonal therapeutics such as anti-estrogens (e.g. Tamoxifen), anti-androgens (e.g. Flutamide or Casodex), LHRH analogs (e.g. Leuprolide, Goserelin or Triptorelin) and aromatase inhibitors.

Other known anti-cancer agents which can be used for combination therapy include bleomycin, retinoids such as all-trans retinoic acid (ATRA), DNA methyltransferase inhibitors such as the 2-deoxycytidine derivative Decitabine (Docagen®), alanosine, cytokines such as interleukin-2 or interferons such as interferon $\alpha 2$ or interferon-$\gamma$, TRAIL, DR4/5 agonistic antibodies, FasL- and TNF-R agonists.

As exemplary chemotherapeutic/anti-cancer agents, which can be useful in the combination therapy according to the present invention the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEXXAR, BICALUTAMIDE, BLEOMYCIN, BROXURIDINE, BUSULFAN, CAPECITABINE, CARBOPLATIN, CARBOQUONE, CARMUSTIN E, CETRORELIX, CHLORAMBUCI L, CHLORMETHINE, CISPLATIN, CLADRIBINE, CLOMIFENE, CYCLOPHOSPHAMIDE, DACARBAZINE, DACLIZUMAB, DACTINOMYCIN, DAUNORUBICIN, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, LANREOTIDE, LETROZOLE, LEUPRORELIN, LOBAPLATIN, LOMUSTINE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PEGASPARGASE, PEGFILGRASTI M, PENTETREOTIDE, PENTOSTATIN, PERFOSFAMI DE, PIPOSULFAN, PIRARUBICIN, PLICAMYCIN, PREDNIMUSTINE, PROCARBAZINE, PROPAGERMANIUM, PROSPIDIUM CHLORIDE, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SPIROMUSTINE, STREPTOZOCIN, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRASTUZUMAB, TREOSULFAN, TRIAZIQUONE, TRIMETREXATE, TRIPTORELIN, TROFOSFAMIDE, UREDEPA, VALRUBICIN, VERTEPORFIN, VINBLASTINE, VINCRISTINE, VINDESINE, VINORELBINE, VOROZOLE, and ZEVALIN.

The person skilled in the art is aware on the base of his/her expert knowledge of the total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously or chronologically staggered (such as e.g. as combined unit dosage forms, as separate unit dosage forms, as adjacent discrete unit dosage forms, as fixed or non-fixed combinations, as kit-of-parts or as admixtures) with one or more known anti-cancer agents or target specific anti-cancer agents, such as e.g. those mentioned above.

In this context, the present invention further relates to a combination comprising a first active ingredient, which is at least one tetrahydropyridothiophene compound according to this invention, and a second active ingredient, which is at least one anti-cancer agent or target specific anti-cancer agent, such as e.g. one or more of those mentioned herein above, for separate, sequential, simultaneous or chronologically staggered use in therapy, such as e.g. to treat, prevent or ameliorate hyperproliferative diseases of benign or malignant behaviour and/or disorders responsive to the induction of apoptosis in a mammal, such as e.g. those diseases mentioned herein, for example cancer.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously or chronologically staggered.

The present invention further relates to a pharmaceutical composition comprising a first active ingredient, which is at least one tetrahydropyridothiophene compound according to this invention, and a second active ingredient, which is at least one anti-cancer agent or target specific anti-cancer agent, such as e.g. one or more of those mentioned herein above, and, optionally, a pharmaceutically acceptable carrier or diluent, for separate, sequential, simultaneous or chronologically staggered use in therapy.

The present invention further relates to a combination product comprising a.) at least one compound according to this invention formulated with a pharmaceutically acceptable carrier or diluent, and b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a tetrahydropyridothiophene compound according to this invention, and a pharmaceutically acceptable carrier or diluent; a preparation of a second active ingredient, which is an art-known anti-cancer and/or target specific anti-cancer agent, such as one of those mentioned above, and a pharmaceutically acceptable carrier or diluent; for simultaneous, sequential, separate or chronologically staggered use in therapy. Optionally, said kit comprises instructions for its use in therapy, e.g. to treat hyperproliferative diseases and/or disorders responsive to the induction of apoptosis, such as e.g. cancer.

The present invention further relates to a combined preparation comprising at least one compound according to the present invention and at least one anti-cancer and/or target specific anti-cancer agent for simultaneous, sequential or separate administration.

The present invention further relates to pharmaceutical combinations or compositions according to this invention having anti-proliferative and/or apoptosis inducing activity.

In addition, the present invention further relates to a method for treating in combination therapy (hyper)proliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating (hyper)proliferative diseases of benign or malignant behaviour and/or disorders responsive to the induction of apoptosis, such as e.g. cancer, in a patient comprising administering in combination therapy separately, simultaneously, sequentially or chronologically staggered a pharmaceutically active and therapeutically effective and tolerable amount of a pharmaceutical composition, which comprises a tetrahydropyridothiophene compound according to this invention and a pharmaceutically acceptable carrier or diluent, and a pharmaceutically active and therapeutically effective and tolerable amount of one or more anti-cancer and/or target specific anti-cancer agents, such as e.g. one or more of those mentioned herein, to said patient in need thereof.

In addition, the present invention further relates to the use of a composition, combination, formulation, preparation or kit according to this invention in the manufacture of a pharmaceutical product, such as e.g. a commercial package or a medicament, for treating, preventing or ameliorating hyperproliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of the present invention together with instructions for simultaneous, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, sequential or separate use with one or more tetrahydropyridothiophene compounds according to the present invention.

The compositions, combinations, preparations, formulations, kits or packages mentioned in the context of the combination therapy according to this invention may also include more than one of the compounds according to this invention and/or more than one of the art-known anti-cancer and/or target specific anti-cancer agents mentioned.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a (hyper)proliferative diseases and/or a disorder responsive to the induction of apoptosis, particularly one of those diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compounds according to this invention and the other active anti-cancer agent in a fixed combination (fixed unit dosage form), or a medicament pack comprising the two active ingredients as discrete separate dosage forms (non-fixed combination). In case of a medicament pack comprising the two active ingredients, the active ingredients are preferably packed into blister cards which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

The administration of the pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous delivery are preferred.

For the treatment of dermatoses, the compounds of the invention are in particular administered in the form of those pharmaceutical compositions which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for apoptosis inducers. Topical application forms (such as ointments) for the treatment of dermatoses thus contain the active compounds in a concentration of, for example, 0.1-99%. The customary dose in the case of systemic therapy (p.o.) is between 0.3 and 30 mg/kg per day, (i.v.) is between 0.3 and 30 mg/kg/h. The choice of the optimal dosage regime and duration of medication, particularly the optimal dose and manner of administration of the active compounds necessary in each case can be determined by a person skilled in the art on the basis of his/her expert knowledge.

Biological Investigations

The anti-proliferative/cytotoxic activity of the compounds described herein, can be tested on subclones of RKO (RKOp27) human colon adenocarcinoma cells (Schmidt et al., Oncogene 19, 2423-2429; 2000) using the Alamar Blue cell viability assay (described in O'Brien et al. Eur J Biochem 267, 5421-5426, 2000). The compounds are dissolved as 20 mM solutions in dimethylsulfoxide (DMSO) and subsequently diluted in semi-logarithmic steps. DMSO dilutions are further diluted 1:100 into Dulbecco's modified Eagle's medium (DMEM) containing 10% fetal calf serum to a final concentration twice as much as the final concentration in the test. RKO subclones are seeded into 96 well flat bottom plates at a density of 4000 cells per well in a volume of 50 µl per well. 24 hours after seeding the 50 µl each of the compound dilutions in DMEM medium are added into each well of the 96 Well plate. Each compound dilution is tested as quadruplicates. Wells containing untreated control cells are filled with 50 µl DMEM medium containing 1% DMSO. The cells are then incubated with the substances for 72 hours at 37° C. in a humified atmosphere containing 5% carbon dioxide. To determine the viability of the cells, 10 µl of an Alamar Blue solution (Biosource) are added and the fluorescence was measured at an extinction of 544 nm and an emission of 590 nm. For the calculation of the cell viability the emission value from untreated cells is set as 100% viability and the emission rates of treated cells were set in relation to the values of untreated cells. Viabilities are expressed as % values.

The corresponding $IC_{50}$ values of the compounds for anti-proliferative/cytotoxic activity are determined from the concentration-effect curves.

Representative $IC_{50}$ values for anti-proliferation/cytotoxicity determined in the aforementioned assay are described in the table A (1st column), in which the numbers of the compound correspond to the numbers of the examples.

Any or all of the compounds according to the present invention which are listed in the Table A, as well as their salts, are to be mentioned as a particular interesting subject of the present invention.

TABLE A

Anti-proliferative/cytotoxic activity

| Compound | IC$_{50}$ RKO p27 uninduced [μM] | IC$_{50}$ RKO p27 induced [μM] |
|---|---|---|
| 1 | 0.5 | >100 |
| 5 | 2 | >100 |
| 6 | 2 | >100 |
| 7 | 2 | >100 |
| 8 | 5 | >100 |
| 10 | 0.2 | >100 |
| 11 | 0.2 | >100 |
| 12, 14, 16, and 17 | The IC50 values of these listed compounds are all ≦3 | The IC50 values of these listed compounds are all >100 |

To determine the cell cycle specific mode of action, subclones of RKO colon adenocarcinoma cells (RKOp27 or RKOp21 as described by Schmidt et al. in Oncogene 19, 2423-2429; 2000) are seeded into 96 well flat bottom plates at a density of 16000 cells per well in a volume of 50 μl per well in DMEM growth medium with 10% FCS containing 10 μM Ponasterone A. 24 hours after seeding the 50 μl each of the compound dilutions in DMEM medium are added into each well of the 96 Well plate. Each compound dilution is tested as quadruplicates. Wells containing untreated control cells are filled with 50 μl DMEM medium containing 1% DMSO. The cells are then incubated with the substances for 72 hours at 37° C. in a humidified atmosphere containing 5% carbon dioxide. To determine the viability of the cells, 10 μl of an Alamar Blue solution (Biosource) are added and the fluorescence was measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values. Viability is compared of proliferating cells grown in the absence of the inducer Ponasterone A, versus viability of cells arrested by the expression of ectopic p27Klp1 induced by Ponasterone A. The data of this experimental setting are summarized in table A (2$^{nd}$ column).

To test the anti-proliferative activity/cytotoxicity on cells known to be highly resistant towards distinct classes of chemotherapeutics, HCT15 cells (with P-glycoprotein overexpression) and MCF7 ADR cells, both of them are known to overexpress certain classes of multidrug resistance transporters are used in Alamar Blue assays as described above. Briefly, the compounds are dissolved as 20 mM solutions in dimethylsulfoxide (DMSO) and subsequently diluted in semi-logarithmic steps. DMSO dilutions were further diluted 1:100 into Dulbecco's modified Eagle's medium (DMEM) containing 10% fetal calf serum to a final concentration twice as much as the final concentration in the test. The cells to be tested are seeded into 96 well flat bottom plates at a density of 10000 cells per well in a volume of 50 μl per well. 24 hours after seeding the 50 μl each of the compound dilutions in DMEM medium are added into each well of the 96 Well plate. Each compound dilution is tested as quadruplicates. Wells containing untreated control cells are filled with 50 μl DMEM medium containing 1% DMSO. The cells are then incubated with the substances for 72 hours at 37° C. in a humidified atmosphere containing 5% carbon dioxide. To determine the viability of the cells, 10 μl of an Alamar Blue solution (Biosource) are added and the fluorescence was measured at an extinction of 544 nm and an emission of 590 nm. For the calculation of the cell viability the emission value from untreated cells is set as 100% viability and the emission rates of treated cells are set in relation to the values of untreated cells. Viabilities are expressed as % values.

The induction of apoptosis can be measured by using a Cell death detection ELISA (Roche Biochemicals, Mannheim, Germany). RKO subclones are seeded into 96 well flat bottom plates at a density of 10000 cells per well in a volume of 50 μl per well. 24 hours after seeding the 50 μl each of the compound dilutions in DMEM medium are added into each well of the 96 Well plate. Each compound dilution is tested at least as triplicates. Wells containing untreated control cells are filled with 50 μl DMEM medium containing 1% DMSO. The cells are then incubated with the substances for 24 hours at 37° C. in a humidified atmosphere containing 5% carbon dioxide. As a positive control for the induction of apoptosis, cells are treated with 50 μM Cisplatin (Gry Pharmaceuticals, Kirchzarten, Germany). Medium is then removed and the cells were lysed in 200 μl lysised buffer. After centrifugation as described by the manufacturer, 10 μl of cell lysate is processed as described in the protocol. The degree of apoptosis is calculated as follows: The absorbance at 405 nm obtained with lysates from cells treated with 50 μM cisplatin is set as 100 cpu (cisplatin units), while an absorbance at 405 nm of 0.0 was set as 0.0 cpu. The degree of apoptosis is expressed as cpu in relation to the value of 100 cpu reached with the lysates obtained from cells treated with 50 μM cisplatin.

The mitotis-confined activity can be measured using a methylen blue/eosin staining kit (Merck, Darmstadt, Germany). RKO subclones are seeded into 6 well tissue culture plates at a density of 200000 cells per well in a volume of 2 ml per well. 24 hours after seeding each of the compound dilutions in DMEM containing up to 1% DMSO are added onto each 6 well plate. The cells are then incubated with the substances for 24 hours at 37° C. in a humidified atmosphere containing 5% carbon dioxide. As a positive control for the induction of mitosis, the cells are treated with 20 nM vincristine or paclitaxel. The cells are then harvested by trypsinization and subsequent centrifugation, and washed once with phosphate-buffered saline. Subsequently, the cells are centrifuged on microscope slides for 1 min at 1200 rpm using a cytospin. Cells are then fixed with methanol and stained with methylen blue and eosin according to the manufacturer's recommendations. Mitotic figures can then be visualized by standard microscopy.

Another method to determine the mitosis confined activity can be immunoblotting of cell extracts with an antibody specific for phosphorylated histone H3, which is a generally accepted marker of mitosis. RKO subclones are seeded into 6 well tissue culture plates at a density of 200000 cells per well in a volume of 2 ml per well. 24 hours after seeding each of the compound dilutions in DMEM containing up to 1% DMSO are added onto each 6 well plate. The cells are then incubated with the substances for another 24 hours at 37° C. in a humidified atmosphere containing 5% carbon dioxide. As a positive control for the induction of mitosis, the cells are treated with 20 nM vincristine or paclitaxel. The cells are then harvested by trypsinization and subsequent centrifugation, and washed once with phosphate-buffered saline. Subsequently, the cells are lysed in a lysis buffer containing 50 mM Tris, pH 7.4, 150 mM NaCl, 1% NP-40, 50 mM NaF, 1 mM Na$_3$VO$_4$, 1 mM phenylmethylsulfonyl fluoride. The lysates are cleared by centrifugation and the supernatants are collected. Equal amounts of lysate protein are separated in an SDS-polyacrylamide electrophoresis using 12.5% gels and subsequently blotted on immobilon membranes (Millipore, schwalbach, Germany). After blocking unspecific binding sites by incubation of the membrane in 3% bovine serum albumine in tris-puffered saline containing 0.05% tween 20, antibodies specific for phospho-histone H3 (Cell Signaling Technology, Beverley, USA) were added for 1 hour. After intensive washing with tris-puffered saline containing 0.05% tween 20, specific signals were visualized using a horseradish-peroxidase-coupled secondary antibody and the use of the ECL chemoluminescence detection kit (Amersham, Braunschweig, Germany) according to the manufacturer's recommendations.

The invention claimed is:
1. A compound of formula I

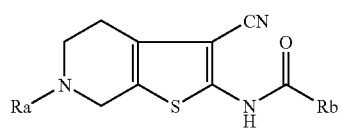

wherein
Ra is —C(O)R1, —C(O)OR2, —C(O)SR2, —C(O)N(R3)R4, —S(O)₂R1, or —S(O)₂N(R3)R4; and
Rb is optionally substituted by Rca and/or Rcb, and is Har, or
Rb is Cyc, or
Rb is chromenyl;
in which
R1, R2 and R3 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or substituted by at least one substituent independently selected from R5;
each R4 is independently selected from the group consisting of: hydrogen, 1-7C-alkyl, and 3-7C-cycloalkyl, wherein each of said 1-7C-alkyl and 3-7C-cycloalkyl can be unsubstituted or substituted by at least one substituent independently selected from R5;
R5, R11 Rca and Rcb may be the same or different and are independently selected from the group consisting of:
1-7C-alkyl, 3-7C-cycloalkyl, Ar, Har, Het, halogen, trifluoromethyl, nitro, cyano, guanidino, amidino, —C(O)R6, —C(O)OR7, —C(O)N(R8)R9, —S(O)₂R6, —S(O)₂N(R8)R9, —N(R10)C(O)R6, —N(R10)C(O)OR7, —N(R10)C(O)N(R8)R9, —N(R10)S(O)₂R6, —N(R10)S(O)₂N(R8)R9, —OC(O)R6, —OC(O)N(R8)R9, —OR7, —N(R8)R(9), and —SR7, wherein each of said 1-7C-alkyl, 3-7C-cycloalkyl, Ar, Har and Het can be unsubstituted or substituted by at least one substituent independently selected from R11;
R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or substituted by at least one substituent independently selected from R12;
each R9 is independently selected from the group consisting of: hydrogen, 1-7C-alkyl, and 3-7C-cycloalkyl, wherein each of said 1-7C-alkyl and 3-7C-cycloalkyl can be unsubstituted or substituted by at least one substituent independently selected from R12;
each R10 is independently selected from the group consisting of: hydrogen, 1-7C-alkyl, and 3-7C-cycloalkyl;
each R12 is independently selected from the group consisting of: R5;
each Ar is independently selected from the group consisting of phenyl and naphthyl;
each Har is independently a fully aromatic or partially aromatic mono- or fused bicyclic ring or ring system made up of a first constituent being a 5- or 6-membered monocyclic unsaturated, aromatic heteroaryl ring A,
which heteroaryl ring A comprises at least one heteroatom independently selected from the group consisting of nitrogen, oxygen and sulfur,
and, optionally, fused to said first constituent,
a second constituent being a benzo group, any 3-7C-cycloalkane group, an additional heteroaryl ring A, or any heterocyclic ring B,
wherein said Har ring or ring system is attached to the parent molecular group via a substitutable ring carbon or ring nitrogen atom;
each Het is independently a fully saturated or partially unsaturated mono- or fused bicyclic ring or ring system made up of a first constituent being a 3- or 7-membered monocyclic fully saturated or partially unsaturated, non-aromatic heterocyclic ring B,
which heterocyclic ring B comprises one to three heteroatoms independently selected from the group consisting of nitrogen, oxygen and sulfur,
and which heterocyclic ring B is optionally substituted by one or two oxo groups,
and, optionally, fused to said first constituent,
a second constituent being a benzo group, any 3-7C-cycloalkane group, or an additional heterocyclic ring B,
wherein said Het ring or ring system is attached to the parent molecular group via a substitutable ring carbon or ring nitrogen atom;
Cyc is a group of formula W

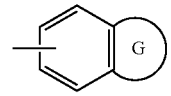

in which
G is optionally substituted by Rda and/or Rdb on a ring carbon atom, and is a 5- or 6-membered saturated heterocyclic ring comprising one or two heteroatoms independently selected from the group consisting of —N(Rdc)—, oxygen and sulfur, in which
Rda is 1-4C-alkyl, or halogen,
Rdb is 1-4C-alkyl, or halogen,
each Rdc is independently selected from the group consisting of: hydrogen, 1-4C-alkyl, and 1-4C-alkylcarbonyl,
wherein said Cyc ring system is attached to the parent molecular group via a substitutable benzoring carbon atom; or a salt thereof.

2. The compound according to claim 1, in which
Ra is —C(O)R1,
in which
R1 is 1-4C-alkyl substituted by R5, in which
R5 is 1-2C-alkoxycarbonyl, 1-2C-alkylcarbonyl, guanidino, carbamoyl, carboxyl, di-1-2C-alkyl-aminocarbonyl, di-1-2C-alkylamino, ureido, 1-2C-alkoxy, hydroxyl, or 1-2C-alkoxyethoxy;
or
Ra is —C(O)OR2,
in which
R2 is 1-4C-alkyl substituted by R5, in which
R5 is 1-2C-alkoxycarbonyl, carboxyl, di-1-2C-alkylaminocarbonyl, di-1-2C-alkylamino, 1-2C-alkoxy, hydroxyl, or 1-2C-alkoxyethoxy;

or
Ra is —C(O)SR2,
in which
R2 is 1-4C-alkyl substituted by R5, in which
R5 is 1-2C-alkoxycarbonyl, carboxyl, di-1-2C-alkylaminocarbonyl, di-1-2C-alkylamino, 1-2C-alkoxy, hydroxyl, or 1-2C-alkoxyethoxy;
or
Ra is —C(O)R1, —C(O)OR2, or —C(O)SR2,
in which
R1, R2 and R3 may be the same or different and are independently selected from the group consisting of: 1-4C-alkyl substituted by R5, in which
R5 is Har, or Het, in which,
in a first alternative,
Har is indolyl, thiophenyl, N-methyl-imidazolyl, methylthiazolyl, or imidazolyl,
or, in a second alternative,
Har is pyridyl, or pyrazinyl,
or, in a third alternative,
Het is piperidinyl, morpholinyl, N-methyl-piperazinyl, or pyrrolidinyl,
or, in a fourth alternative,
Het is 1,3-benzodioxolyl,
or
R1, R2 and R3 may be the same or different and are independently selected from the group consisting of:
1-7C-alkyl;
or salt thereof.

3. The compound according to claim 1, in which
Ra is —C(O)R1, in which
R1 is methyl, propyl, hexyl, R5-substituted propyl, or R5-substituted ethyl, in which
R5 is carbamoyl, methoxy, methoxycarbonyl or acetyl, indol-2-yl, or thiophen-2-yl;
or
Ra is —C(O)OR2, in which
R2 is methyl, ethyl, tertbutyl, pentyl, or R5-substituted ethyl, in which
R5 is methoxy, or 4-methyl-thiazol-5-yl;
or
Ra is —C(O)SR2, in which
R2 is ethyl;
or a salt thereof.

4. The compound according to claim 1,
in which
Ra is —C(O)OR2, in which
R2 is ethyl;
or a salt thereof.

5. The compound according to claim 1,
in which,
in a first embodiment,
Rb is optionally substituted by Rca and/or Rcb, and is Har, in which
Har is a 5-membered monocyclic unsaturated, aromatic heteroaryl radical comprising at least one heteroatom independently selected from the group consisting of oxygen, nitrogen and sulfur,
or
Har is a 6-membered monocyclic unsaturated, aromatic heteroaryl radical comprising one or two nitrogen atoms,
or
Har contains optionally a benzene ring moiety, and is a 10-membered fused bicyclic unsaturated, aromatic heteroaryl radical comprising at least one heteroatom independently selected from the group consisting of oxygen, nitrogen and sulfur,
or
Har contains optionally a benzene ring moiety, and is a 11-membered fused bicyclic unsaturated, aromatic heteroaryl radical comprising at least one heteroatom independently selected from the group consisting of oxygen, nitrogen and sulfur,
wherein said Har ring or ring system is attached to the parent molecular group via a substitutable ring carbon atom,
and in which
Rca is 1-4C-alkyl, halogen, phenyl, nitro, or phenylsulfonyl,
Rcb is 1-4C-alkyl, and halogen;
or,
in a second embodiment,
Rb is Cyc, in which
Cyc is 1,3-benzodioxolyl, 2,3-dihydro-1,4-benzodioxinyl, or 2,3-dihydrobenzofuranyl, wherein said Cyc ring system is attached to the parent molecular group via a substitutable benzoring carbon atom;
or,
in a third embodiment,
Rb is chromenyl;
or a salt thereof.

6. The compound according to claim 1,
in which
Rb is selected from the group consisting of 3-methyl-5-phenyl-isoxazol-4-yl, 3-phenyl-5-methyl-isoxazol-4-yl, thiophenyl, benzothiophenyl, benzofuranyl, pyridyl, pyrazinyl, (methyl)-thiophenyl, 1,3-benzodioxol-5-yl, 1,3-benzodioxol-4-yl, 2,3-dihydro-1,4-benzodioxin-5-yl, 2,3-dihydro-1,4-benzodioxin-6-yl, 2,3-dihydro-benzofuran-4-yl, 2,3-dihydro-benzofuran-5-yl, 2,3-dihydro-benzofuran-6-yl, 2,3-dihydro-benzofuran-7-yl and chromenyl;
or a salt thereof.

7. The compound according to claim 1,
in which
Rb is pyridin-3-yl, 5-methyl-thiophen-2-yl, 2,3-dihydrobenzofuran-6-yl, or benzofuran-6-yl,
or a salt thereof.

8. The compound of formula I according to claim 1,
in which
Ra is —C(O)R1, in which
R1 is 1-6C-alkyl,
or
R1 is 1-4C-alkyl which is mono-substituted by R5, in which
R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, phenyl, 1-4C-alkoxycarbonyl, carboxyl, amino, morpholino, piperidino, pyrrolidino, 4N-(1-4C-alkyl)-piperazino, mono- or di-1-4C-alkylamino, mono- or di-1-4C-alkylaminocarbonyl, carbamoyl, ureido, guanidino, imidazolo, triazolo, pyrazolo, 1-4C-alkylcarbonyloxy or 1-4C-alkylcarbonylamino,
wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N-(1-4C-alkyl)-pyrazolyl, imidazolo, pyrazolo or phenyl radicals alone or part of another group may be unsubstituted or optionally substituted by one or two substituents independently selected from the group consisting of halogen, 1-4C-alkoxy, nitro and 1-4C-alkyl, or R1 is 3-4C-alkyl which is substituted by two hydroxyl groups on different carbon atoms, or R1 is 1-2C-alkyl which is substituted by 2,2-dimethyl-[1,3]dioxolan-4-yl;

or in which

Ra is —C(O)OR2, in which

R2 is 1-6C-alkyl, or

R2 is 1-4C-alkyl which is mono-substituted by R5, in which

R5 is pyridyl, pyrimidinyl, pyrazinyl, indolyl, benzofuranyl, benzothiophenyl, thiazolyl, oxazolyl, 1N-(1-4C-alkyl)-imidazolyl, 1N- (1-4C-alkyl)-pyrazolyl, phenyl, 1-4C-alkoxycarbonyl, carboxyl, mono- or di-1-4C-alkylaminocarbonyl or carbamoyl, wherein each of said pyridyl, pyrimidinyl, pyrazinyl, indolyl, benzofuranyl, benzothiophenyl, thiazolyl, oxazolyl, 1N-(1-4C-alkyl)-imidazolyl, 1N- (1-4C-alkyl)-pyrazolyl or phenyl radicals can be unsubstituted or substituted by one or two substituents independently selected from the group consisting of halogen, 1-4C-alkoxy, nitro and 1-4C-alkyl, or R2 is 2-4C-alkyl which is mono-substituted by R5, in which R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkylcarbonylamino, wherein each of said imidazolo, pyrazolo or phenyl radicals alone or part of another group can be unsubstituted or substituted by one or two substituents independently selected from the group consisting of halogen, 1-4C-alkoxy, nitro and 1-4C-alkyl, or R2 is 3-4C-alkyl which is substituted by two hydroxyl groups on different carbon atoms, or R2 is 1-2C-alkyl which is substituted by 2,2-dimethyl-[1,3]dioxolan-4-yl;

or in which

Ra is —C(O)SR2, in which

R2 is 1-6C-alkyl, or

R2 is 1-4C-alkyl which is mono-substituted by R5, in which

R5 is pyridyl, pyrimidinyl, pyrazinyl, indolyl, benzofuranyl, benzothiophenyl, thiazolyl, oxazolyl, 1N-(1-4C-alkyl)-imidazolyl, 1N- (1-4C-alkyl)-pyrazolyl, phenyl, 1-4C-alkoxycarbonyl, carboxyl, mono- or di-1-4C-alkylaminocarbonyl or carbamoyl, wherein each of said pyridyl, pyrimidinyl, pyrazinyl, indolyl, benzofuranyl, benzothiophenyl, thiazolyl, oxazolyl, 1N- (1-4C-alkyl)-imidazolyl, 1N- (1-4C-alkyl)-pyrazolyl or phenyl radicals can be unsubstituted or optionally substituted by one or two substituents independently selected from the group consisting of halogen, 1-4C-alkoxy, nitro and 1-4C-alkyl, or R2 is 2-4C-alkyl which is mono-substituted by R5, in which R5 is 1-4C-alkoxy, 1-4C-alkoxy-2-4C-alkoxy, (1-4C-alkoxy-2-4C-alkoxy)-2-4C-alkoxy, hydroxyl, phenyl-1-4C-alkoxy, phenoxy, amino, morpholino, piperidino, pyrrolidino, 4N-(1-4C-alkyl)-piperazino, mono- or di-1-4C-alkylamino, ureido, guanidino, imidazolo, triazolo, pyrazolo, 1-4C-alkylcarbonyloxy or 1-4C-alkylcarbonylamino, wherein each of said imidazolo, pyrazolo or phenyl radicals alone or part of another group can be unsubstituted or substituted by one or two substituents independently selected from the group consisting of halogen, 1-4C-alkoxy, nitro and 1-4C-alkyl;

and in which

Rb is optionally substituted by Rca and/or Rcb, and is Har, or

Rb is Cyc, or

Rb is chromenyl, in which

Har is a 5-membered monocyclic heteroaryl radical comprising one, two or three nitrogen atoms and/or one heteroatom independently selected from the group consisting of oxygen and sulphur, or a 6-membered monocyclic heteroaryl radical comprising one or two nitrogen atoms, or a 9-membered fused bicyclic heteroaryl radical comprising one, two or three heteroatoms independently selected from the group consisting of nitrogen, oxygen and sulphur, or a 10-membered fused bicyclic heteroaryl radical comprising one, two or three heteroatoms independently selected from the group consisting of nitrogen, oxygen and sulphur, wherein said Har radical is attached to the parent molecular group via a ring carbon atom, Cyc is 1,3-benzodioxolyl, 2,3-dihydro-1,4-benzodioxinyl, 2,2-difluoro-1,3-benzodioxolyl, 2,2-dimethyl-1,3-benzodioxolyl, chromanyl or 2,3-dihydro-benzofuranyl, wherein said Cyc ring system is attached to the parent molecular group via a substitutable benzoring carbon atom, Rca is halogen, 1-4C-alkyl, 1-4C-alkoxy, phenyl, phenoxy or morpholino, Rcb is halogen, 1-4C-alkyl or 1-4C-alkoxy;

or a salt thereof.

9. The compound of formula I according to claim 1 in which

Ra is —C(O)R1, in which

R1 is methyl, ethyl, propyl or butyl, or

R1 is methyl which is mono-substituted by R5, ethyl which is mono-substituted by R5, or propyl which is mono-substituted by R5, in which R5 is methoxy, ethoxy, 2-methoxyethoxy, 2-(2-methoxyethoxy)-ethoxy, hydroxyl, pyridyl, pyrimidinyl, pyrazinyl, indolyl, thiazolyl, oxazolyl, 1N-methyl-imidazolyl, 1N-methyl-pyrazolyl, phenyl, methoxycarbonyl, ethoxycarbonyl, carboxyl, dimethylaminocarbonyl, morpholino, carbamoyl, ureido, guanidino, imidazolo, triazolo, pyrazolo, ethylcarbonyloxy or methylcarbonyloxy, or
R1 is propyl or butyl, each of which is substituted by two hydroxyl groups on different carbon atoms,
or
R1 is methyl or ethyl, each of which is substituted by 2,2-dimethyl-[1,3]dioxolan-4-yl;
or in which
Ra is —C(O)OR2, in which
R2 is methyl, ethyl, propyl or butyl,
or
R2 is cyclohexyl, phenyl, pyridyl, (1-2C-alkoxycarbonyl)-phenyl, or (1-2C-alkoxy)-phenyl,
or
R2 is methyl which is mono-substituted by R5, ethyl which is mono-substituted by R5, or propyl which is mono-substituted by R5, in which
R5 is pyridyl, pyrimidinyl, pyrazinyl, 1N-methyl-imidazolyl, 1N-methyl-pyrazolyl, phenyl, (1-2C-alkoxy)-phenyl, methoxycarbonyl, ethoxycarbonyl, carboxyl, di-methylaminocarbonyl or carbamoyl,
or
R2 is ethyl which is mono-substituted by R5, or propyl which is mono-substituted by R5, in which
R5 is methoxy, ethoxy, 2-methoxyethoxy, 2-(2-methoxyethoxy)-ethoxy, hydroxyl, benzyloxy, phenoxy, morpholino, piperidino, pyrrolidino, 4N-(methyl)-piperazino, dimethylamino, imidazolo, triazolo, pyrazolo, methylcarbonyloxy, ethylcarbonyloxy, methylcarbonylamino or ethylcarbonylamino,
or
R2 is propyl or butyl, each of which is substituted by two hydroxyl groups on different carbon atoms,
or
R2 is methyl or ethyl, each of which is substituted by 2,2-dimethyl-[1,3]dioxolan-4-yl;
or in which
Ra is —C(O)SR2, in which
R2 is methyl, ethyl, propyl, butyl or pentyl,
or
R2 is methyl which is mono-substituted by R5, ethyl which is mono-substituted by R5, or propyl which is mono-substituted by R5, in which
R5 is pyridyl,
or
R2 is ethyl which is mono-substituted by R5, or propyl which is mono-substituted by R5, in which
R5 is hydroxyl, methoxy or ethoxy;
and in which
Rb is substituted by Rca, and is thiophenyl, furanyl, pyridyl or (phenyl)-isoxazolyl,
or
Rb is unsubstituted, and is thiophenyl, furanyl, pyridyl, benzofuranyl or benzothiophenyl,
or
Rb is 1,3-benzodioxol-5-yl, 1,3-benzodioxol-4-yl, 2,2-difluoro-1,3-benzodioxol-5-yl, 2,2-difluoro-1,3-benzodioxol-6-yl, 2,3-dihydro-1,4-benzodioxin-5-yl, 2,3-dihydro-1,4-benzodioxin-6-yl, 2,3-dihydro-benzofuran-4-yl, 2,3-dihydro-benzofuran-5-yl, 2,3-dihydro-benzofuran-6-yl or 2,3-dihydro-benzofuran-7-yl,
or
Rb is chromenyl,
in which
Rca is methyl or ethyl;
or a salt thereof.
10. The compound of formula I according to claim 1, in which
Ra is —C(O)R1, in which
R1 is methyl, ethyl or propyl,
or
R1 is (R5)-methyl, 2-(R5)-ethyl, or 3-(R5)-propyl, in which
R5 is methoxy, ethoxy, 2-methoxyethoxy, 2-(2-methoxyethoxy)-ethoxy, hydroxyl, pyridyl, pyrimidinyl, pyrazinyl, imidazolo, pyrazolo or methylcarbonyloxy,
or
R1 is 2,3-dihydroxy-propyl;
or in which
Ra is —C(O)OR2, in which
R2 is methyl, ethyl or propyl,
or
R2 is (R5)-methyl, 2-(R5)-ethyl, or 3-(R5)-propyl, in which
R5 is pyridyl, pyrazinyl or pyrimidinyl,
or
R2 is 2-(R5)-ethyl, or 3-(R5)-propyl, in which
R5 is methoxy, ethoxy, 2-methoxyethoxy, 2-(2-methoxyethoxy)-ethoxy, hydroxyl, imidazolo, pyrazolo or methylcarbonyloxy,
or
R2 is 2,3-dihydroxy-propyl;
or in which
Ra is —C(O)SR2, in which
R2 is methyl, ethyl or propyl,
or
R2 is (R5)-methyl, 2-(R5)-ethyl, or 3-(R5)-propyl, in which
R5 is pyridyl,
or
R2 is 2-(R5)-ethyl, or 3-(R5)-propyl, in which
R5 is hydroxyl;
and in which
Rb is substituted by Rca, and is thiophenyl or furanyl,
or
Rb is unsubstituted, and is thiophenyl, furanyl, pyridyl, benzofuran-4-yl, benzofuran-5-yl, benzofuran-6-yl or benzofuran-7-yl,
or
Rb is 1,3-benzodioxol-5-yl, 1,3-benzodioxol-4-yl, 2,3-dihydro-1,4-benzodioxin-5-yl, 2,3-dihydro-1,4-benzodioxin-6-yl, 2,3-dihydro-benzofuran-4-yl, 2,3-dihydro-benzofuran-5-yl, 2,3-dihydro-benzofuran-6-yl or 2,3-dihydro-benzofuran-7-yl,
in which
Rca is methyl;
or a salt thereof.
11. The compound of formula I according to claim 1 in which
Ra is —C(O)OR2, in which
R2 is ethyl,
or in which
Ra is —C(O)SR2, in which
R2 is ethyl;
and in which
Rb is substituted by methyl, and is thiophen-2-yl or thiophen-3-yl,
or
Rb is pyridin-2-yl, pyridin-3-yl, pyridin-4-yl, benzofuran-4-yl, benzofuran-5-yl, benzofuran-6-yl or benzofuran-7-yl,
or
Rb is 2,3-dihydro-benzofuran-4-yl, 2,3-dihydro-benzofuran-5-yl, 2,3-dihydro-benzofuran-6-yl or 2,3-dihydro-benzofuran-7-yl,
or a salt thereof.

12. A pharmaceutical composition comprising one or more compounds according to claim 1, or a pharmaceutically acceptable salt thereof, together with a pharmaceutically acceptable excipient and/or vehicle.

13. The compound of formula I according to claim 1 in which Rb is 5-methyl-thiophen-2-yl.

14. The compound of formula I according to claim 1 in which Har is furanyl, thiophenyl, pyrrolyl, oxazolyl, isoxazolyl, thiazolyl, isothiazolyl, imidazolyl, pyrazolyl, triazolyl, thiadiazolyl, oxadiazolyl, pyridinyl, pyrimidinyl, pyrazinyl, pyridazinyl, quinazolinyl, quinoxalinyl, cinnolinyl, quinolinyl, isoquinolinyl, indolyl, isoindolyl, indazolyl, phthalazinyl, benzothiophenyl, benzofuranyl, isobenzofuranyl, benzoxazolyl, benzothiazolyl, benzimidazolyl, benzotriazolyl, benzoxadiazolyl, benzothiadiazolyl, naphthyridinyl, indolizinyl or purinyl.

15. The compound of formula I according to claim 1 in which
R5, Rca and Rcb may be the same or different and are independently selected from the group consisting of:
1-7C-alkyl, 3-7C-cycloalkyl, Ar, Har, Het, halogen, trifluoromethyl, nitro, cyano, guanidino, amidino, —C(O)R6, —C(O)OR7, —C(O)N(R8)R9, —N(R10)C(O)R6, —N(R10)C(O)OR7, —N(R10)C(O)N(R8)R9, —N(R10)S(O)$_2$R6, —N(R10)S(O)$_2$N(R8)R9, —OC(O)R6, —OC(O)N(R8)R9, —OR7, —N(R8)R(9), and —SR7, wherein each of said 1-7C-alky, 3-7C-cycloalkyl, Ar, Har and Het can be unsubstituted or optionally substituted by at least one substituent independently selected from R11.

16. A compound of formula I

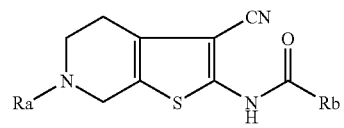

(I)

wherein
Ra is —C(O)R1, —C(O)OR2, —C(O)SR2, —C(O)N(R3)R4, —S(O)$_2$R1, or —S(O)$_2$N(R3)R4; and
Rb is optionally substituted by Rca and/or Rcb, and is Har, or
Rb is Cyc,
or
Rb is chromenyl;
in which
R1, R2 and R3 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or substituted by at least one substituent independently selected from R5;
each R4 is independently selected from the group consisting of: hydrogen, 1-7C-alkyl, and 3-7C-cycloalkyl, wherein each of said 1-7C-alkyl and 3-7C-cycloalkyl can be unsubstituted or substituted by at least one substituent independently selected from R5;
R5, Rca and Rcb may be the same or different and are independently selected from the group consisting of
1-7C-alkyl, 3-7C-cycloalkyl, Ar, Har, Het, halogen, trifluoromethyl, nitro, cyano, guanidino, amidino, —C(O)R6, —C(O)OR7, —C(O)N(R8)R9, —S(O)$_2$R6, —S(O)$_2$N(R8)R9, —N(R10)C(O)R6, —N(R10)C(O)OR7, —N(R10)C(O)N(R8)R9, —N(R10)S(O)$_2$R6, —N(R10)S(O)$_2$N(R8)R9, —OC(O)R6, —OC(O)N(R8)R9, —OR7, —N(R8)R(9), and —SR7, wherein each of said 1-7C-alkyl, 3-7C-cycloalkyl, Ar, Har and Het can be unsubstituted or substituted by at least one substituent independently selected from R11;
R6, R7 and R8 may be the same or different and are independently selected from the group consisting of: hydrogen, 1-7C-alkyl, 3-7C-cycloalkyl, Ar, Har and Het, wherein each of said 1-7C-alkyl, 3-7C-cycloalkyl, Ar, Har and Het can be unsubstituted or substituted by at least one substituent independently selected from R12;
each R9 is independently selected from the group consisting of hydrogen, 1-7C-alkyl, and 3-7C-cycloalkyl, wherein each of said 1-7C-alkyl and 3-7C-cycloalkyl can be unsubstituted or substituted by at least one substituent independently selected from R12;
each R10 is independently selected from the group consisting of: hydrogen, 1-7C-alkyl, and 3-7C-cycloalkyl;
R11 is selected from the group consisting of R5;
each R12 is independently selected from the group consisting of: R5;
each Ar is independently selected from the group consisting of phenyl and naphthyl;
each Har is independently a fully aromatic or partially aromatic mono- or fused bicyclic ring or ring system made up of a first constituent being a 5- or 6-membered monocyclic unsaturated, aromatic heteroaryl ring A,
which heteroaryl ring A comprises at least one heteroatom independently selected from the group consisting of nitrogen, oxygen and sulfur,
and, optionally, fused to said first constituent,
a second constituent being a benzo group, a 3-7C-cycloalkane group, an additional heteroaryl ring A, or a heterocyclic ring B,
wherein said Har ring or ring system is attached to the parent molecular group via a substitutable ring carbon or ring nitrogen atom;
each Het is independently a fully saturated or partially unsaturated mono- or fused bicyclic ring or ring system made up of
a first constituent being a 3- or 7-membered monocyclic fully saturated or partially unsaturated, non-aromatic heterocyclic ring B,
which heterocyclic ring B comprises one to three heteroatoms independently selected from the group consisting of nitrogen, oxygen and sulfur,
and which heterocyclic ring B is optionally substituted by one or two oxo groups,
and, optionally, fused to said first constituent,
a second constituent being a benzo group, a 3-7C-cycloalkane group, or an additional heterocyclic ring B,
wherein said Het ring or ring system is attached to the parent molecular group via a substitutable ring carbon or ring nitrogen atom;
Cyc is a group of formula W

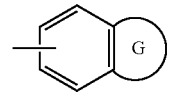

(W)

in which
G is optionally substituted by Rda and/or Rdb on a ring carbon atom, and is a 5-or 6-membered saturated heterocyclic ring comprising one or two heteroatoms independently selected from the group consisting of —N(Rdc)-, oxygen and sulfur, in which
Rda is 1-4C-alkyl, or halogen,
Rdb is 1-4C-alkyl, or halogen,
each Rdc is independently selected from the group consisting of: hydrogen, 1-4C-alkyl, and 1-4C-alkylcarbonyl,
wherein said Cyc ring system is attached to the parent molecular group via a substitutable benzoring carbon atom.

17. A pharmaceutical composition comprising one or more compounds according to claim 16, together with a pharmaceutically acceptable excipient and/or vehicle.

18. The compound of formula I according to claim 16 in which

R5, Rca and Rcb may be the same or different and are independently selected from the group consisting of:
1-7C-alkyl, 3-7C-cycloalkyl, Ar, Har, Het, halogen, trifluoromethyl, nitro, cyano, guanidino, amidino, —C(O)R6, —C(O)OR7, —C(O)N(R8)R9, —N(R10)C(O)R6, —N(R10)C(O)OR7, —N(R10)C(O)N(R8)R9, —N(R10)S(O)$_2$R6, —N(R10)S(O)$_2$N(R8)R9, —OC(O)R6, —OC(O)N(R8)R9, —OR7, —N(R8)R(9), and —SR7, wherein each of said 1-7C-alkyl, 3-7C-cycloalkyl, Ar, Har and Het can be unsubstituted or optionally substituted by at least one substituent independently selected from R11.

* * * * *

UNITED STATES PATENT AND TRADEMARK OFFICE
CERTIFICATE OF CORRECTION

PATENT NO. : 7,517,986 B2
APPLICATION NO. : 11/597556
DATED : April 14, 2009
INVENTOR(S) : Pekari et al.

It is certified that error appears in the above-identified patent and that said Letters Patent is hereby corrected as shown below:

Column 54, line 26, reads "a second constituent being a benzo group, any 3-7C-cy-" should read -- a second constituent being a benzo group, a 3-7C-cy- --

Column 57, line 65 reads "tuted or optionally substituted by one or two substitu-" should read -- tuted or substituted by one or two substitu- --

Column 62, line 12 reads "ing of hydrogen, l-7C-alkyl, and 3-7C-cycloalkyl," should read -- ing of: hydrogen, 1-7C-alkyl, and 3-7C-cycloalkyl, --

Signed and Sealed this
Eighth Day of March, 2011

David J. Kappos
*Director of the United States Patent and Trademark Office*